United States Patent [19]
Ali et al.

[11] Patent Number: 6,107,332
[45] Date of Patent: *Aug. 22, 2000

[54] HYDROLYSIS-PROMOTING HYDROPHOBIC TAXANE DERIVATIVES

[75] Inventors: Shaukat Ali, Monmouth Junction; J. Craig Franklin, Skillman; Imran Ahmad, Cranbury; Eric Mayhew, Monmouth Junction; Soumendu Bhattacharya, Plainsboro; Gil Koehane, Piscataway, all of N.J.; Andrew S. Janoff, Yardley, Pa.

[73] Assignee: The Liposome Company, Inc., Princeton, N.J.

[*] Notice: This patent is subject to a terminal disclaimer.

[21] Appl. No.: 09/249,004

[22] Filed: Feb. 12, 1999

Related U.S. Application Data

[63] Continuation-in-part of application No. 08/805,184, Feb. 27, 1997, which is a continuation-in-part of application No. 08/712,684, Sep. 12, 1996, Pat. No. 5,703,117.
[60] Provisional application No. 60/003,575, Sep. 12, 1995.
[51] Int. Cl.$^7$ .................. A61K 31/337; C07D 305/14
[52] U.S. Cl. ................ 514/449; 510/510; 510/511
[58] Field of Search .................. 549/510, 511; 514/449

[56] References Cited

U.S. PATENT DOCUMENTS 5,703,117  12/1997  Mayhew et al. .................. 514/449

OTHER PUBLICATIONS

McLaughlin, et al., "19–Hydroxybaccatin III, 10–Deacetyl-cephalomannine, and 10–Deacetyltaxol: New anti–tumor Taxanes from *Taxus Wallichiana*," J. Nat Prod., 44(3), 312–319, 1981.

*Primary Examiner*—Ba K. Trinh
*Attorney, Agent, or Firm*—Rosanne Goodman

[57] ABSTRACT

Provided herein is a taxane having a hydrocarbon attached at the 2' and/or 7 positions, the hydrocarbon's alpha position being occupied by a "hydrolysis-promoting group" ("HPG"). In one embodiment, the hydrolysis promoting group is stereospecifically attached to the α-carbon of the hydrophobic taxane. The Substitution of an HPG for the methylene unit ordinarily occupying the alpha position allows for enhanced in vivo hydrolysis of the hydrocarbon-taxane bond, and hence, for enhanced taxane therapeutic activity. Also provided herein are taxane-containing compositions, and methods of administering taxanes to animals, including those afflicted with cancers or inflammatory diseases.

69 Claims, 14 Drawing Sheets

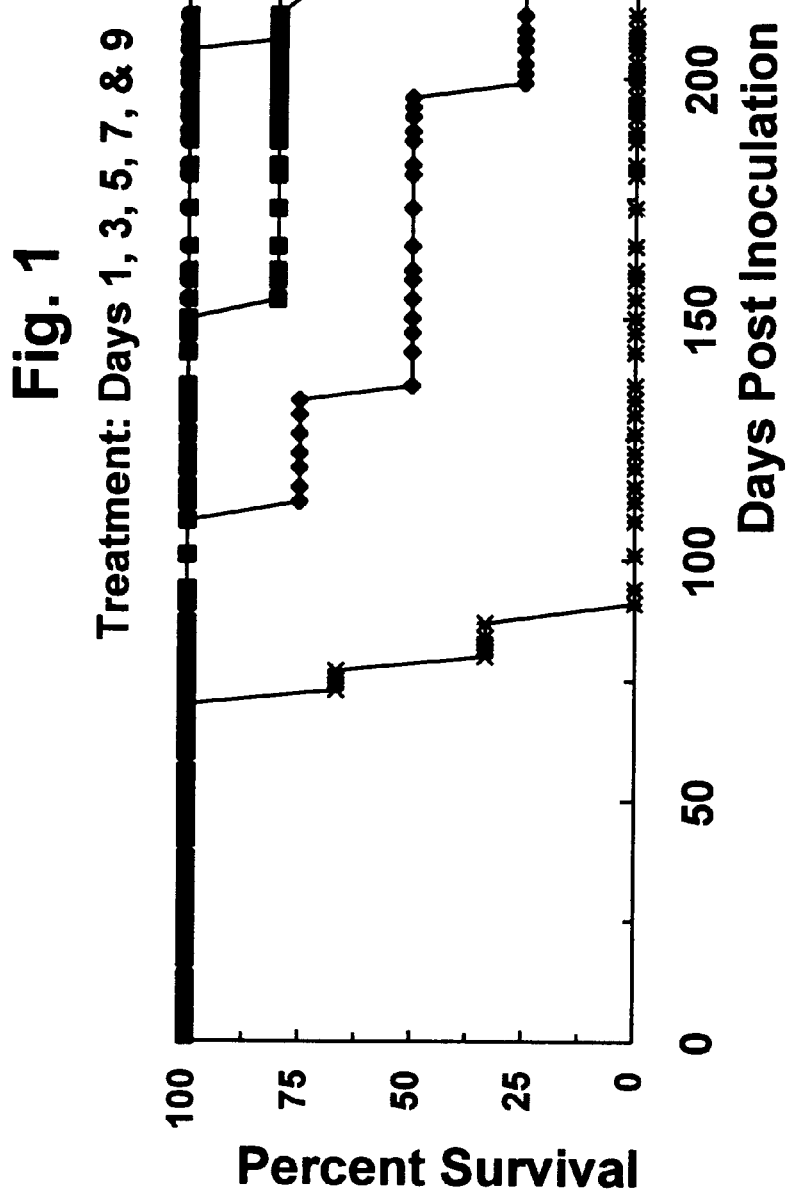

Time in hrs

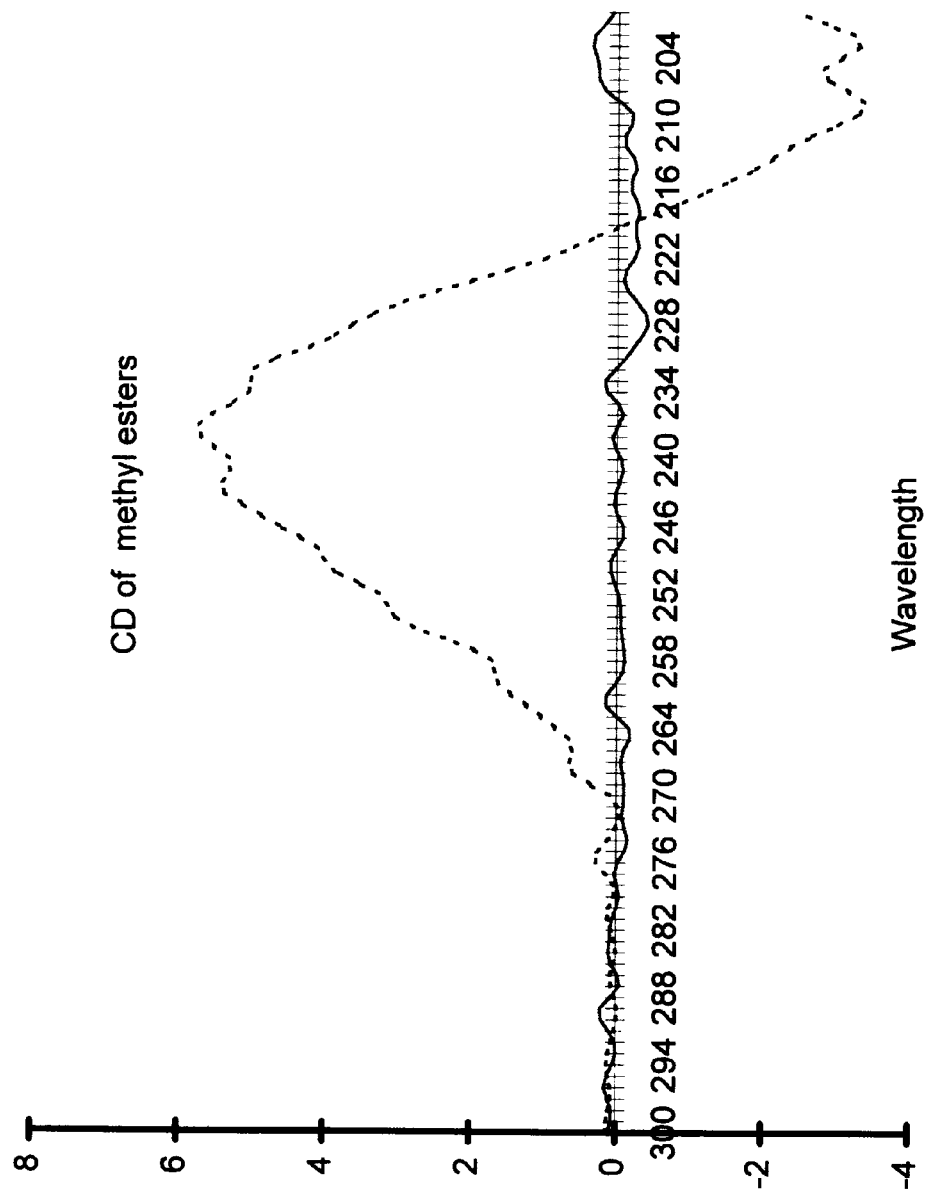

HYDROLYSIS-PROMOTING HYDROPHOBIC TAXANE DERIVATIVES

This application is a continuation-in-part (CIP) of our copending U.S. patent application Ser. No. 08/805,184 filed Feb. 27, 1997, pending which in turn is a CIP of our U.S. patent application Ser. No. 08/712,684, filed Sep. 12, 1996, which is now issued as U.S. Pat. No. 5,703,117, which claims the benefit of U.S. Provisional Application No. 60/003,575, filed Sep. 12, 1995 and now abandoned.

FIELD OF THE INVENTION

This invention provides compounds which are a taxane to which an acyl chain has been attached; the acyl chain has been derivatized by the stereospecific attachment thereto of a hydrolysis-promoting group. Also provided herein are compositions comprising such compounds and racemic mixtures thereof, including lipid carrier-containing pharmaceutical compositions, and methods of administering such compositions to animals, such as humans afflicted with cancers or certain inflammatory conditions.

BACKGROUND OF THE INVENTION

Taxanes can be isolated from natural sources, and can also be prepared synthetically from naturally occurring precursors. Paclitaxel (TAXOL®, Bristol-Myers Squibb), for example, can be prepared from baccatin by attachment of protecting groups to the hydroxyl groups of baccatin that are to become the hydroxyl groups of paclitaxel, converting the precursor baccatin to paclitaxel, and then removing the protecting groups from the hydroxyl groups to obtain paclitaxel. In addition, paclitaxel has recently been synthesized from simple precursors. (See, e.g., WO93/10076, int. pub. date May 27, 1993; K. V. Rao, U.S. Pat. No. 5,200,534; R. A. Holton, U.S. Pat. No. 5,015,744; PCT/US92/07990; V. J. Stella and A. E. Mathew, U.S. Pat. No. 4,960,790; K. C. Nicolau, Nature 364 (1993), pp. 464–466; Nicolau, K. C. et al. Nature 367 (1994) pp.630–634; Holton, R. A., et al. J. Am. Chem. Soc. 116 (1994) pp. 1597–1600; WO93/16059, int. pub. date Aug. 19, 1993; EP 528,729, published Feb. 24, 1993; EP 522,958, published Jan. 13, 1993; WO91/13053, int. pub. date Sep. 5, 1991; EP 414,610, int. pub. date Feb. 27, 1991; the contents of these documents are incorporated herein by reference).

Taxanes can be used effectively to treat a variety of cancers and recently has been reported to have therapeutic effects in treating certain inflammatory diseases. Paclitaxel, for example, has been found to have activity against ovarian and breast cancers, as well as against malignant melanoma, colon cancer, leukemias and lung cancer (see, e.g., Borman, Chemical & Engineering News, Sep. 2, 1991, pp. 11–18; The Pharmacological Basis of Therapeutics (Goodman Gilman et al., eds.), Pergamon Press, New York (1990), p. 1239; Suffness, Antitumor Alkaloids, in: "The Alkaloids, Vol. XXV," Academic Press, Inc. (1985), Chapter 1, pp. 6–18; Rizzo et al., J. Pharm. & Biomed. Anal. 8(2):159–164 (1990); and Biotechnology 9:933–938 (October, 1991). Paclitaxel has been hypothesized to act against cancer cells by binding to tubulin in the cells' nuclei, thereby blocking the disassembly of microtubules and consequently, inhibiting cell division (Schiff et al., Nature 277:665 (1979).

However, formulation of taxanes in therapeutically useful carriers, so as to enable the taxanes to be administered to animals, is made difficult by the nature of the taxane molecules, which can be poorly soluble in both aqueous and lipid carriers. Paclitaxel, for example, is currently supplied as a formulation of polyoxyethylated derivative of castor oil, Cremophor EL® and ethanol (50:50) because of its lack of significant aqueous or liposome solubility. However, the Cremophor EL® carrier itself can cause toxic side effects or increase the side effects caused by the taxane when administered to animals. Thus, administration of the Cremophor EL®:ethanol-based paclitaxel formulation generally entails premedication with other drugs, as well as a slow infusion of a large volume of the formulation, thus often necessitating over night hospital stays and their attendant costs. Alternatively, a stable formulation of a taxane with a lower concentration of a polyoxyethylated derivative of castor oil could be important in reducing the toxic side effects of the drug product.

Compositions provided herein provide taxanes in the form of compounds which are taxanes to which an acyl chain has been attached. The acyl chain enhances the taxane's lipid solubility. Thus, the taxane can be stably associated with a lipid-based carrier such as a liposome, for an extended period of time. However, the compositions provided herein may also be administered in non-liposomal carriers, such as USP/NF Polyoxyl 35 Castor Oil. The acyl chain itself has been derivatized by the attachment thereto of a hydrolysis-promoting group, which is a chemical moiety that promotes hydrolysis of the derivatized acyl chain from the parent taxane, once the taxane has been disassociated from the lipid-based carrier, so as to give the parent taxane in a therapeutically useful form. The hydrolysis-promoting group may take the structure of a single enantiomer or may be administered as a mixture of (S) and (R) enantiomers. There may be a stereospecific difference in the biological and pharmacological activity attributable to the enantiomeric form. While not being limited to this explanation, it is possible that in vivo cleavage may favor one enantiomer. Thus, by providing a method to deliver the preferred enantiomeric form of the hydrolyzable hydrophobic taxane of the present invention, administeration of lower dosage than with mixed racemic forms may provide equivalent therapeutic effect. The present invention, therefore, additionally provides methods for preparing single enantiomeric forms of the hydrolyzable hydrophobic acyl chains and methods for synthesizing the hydrolyzable hydrophobic taxane having a single enantiomeric substituted fatty acid or at least enriched in a single enantiomeric form.

The compounds provided herein can be administered to animals as such, or may be formulated together with a lipid-based carrier prior to administration. Such formulations may enhance delivery of the taxane to its intended site of action in an animal and may alter the pharmacological action by delaying the release of the therapeutic agent in the animal or may delay the clearance of the therapeutic agent from the animal. These formulations may therefore allow increased time of exposure of the animal to the therapeutic agent. However, the drug compound comprising the HPG must be stable in formulations until administration.

SUMMARY OF THE INVENTION

This invention provides a taxane having the formula:

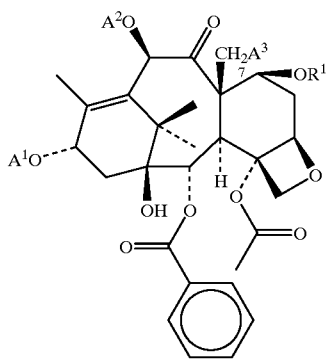

wherein: $A^1$ is H or a group having the formula Z—C(O)NHCH($C_6H_5$)CH(OR)C(O)—; Z is $C_6H_5$—, $C_6H_5CH_2$—O—, $C(CH_3)_3$—O— or $CH(CH_3)$=$C(CH_3)$—; $A^2$ is H or $CH_3C(O)$—; and $A^3$ is H or OH. Each of R and $R^1$ is H or a group having the formula $Y^1Y^2$, provided that at least one of R and $R^1$ is not H, $Y^1$ is a group having the formula —C(O)CHX$^1$(CH$_2$)$_{n1}$(CH=CH)$_{n2}$(CH$_2$)$_{n3}$(CH=CH)$_{n4}$ (CH$_2$)$_{n5}$(CH=CH)$_{n6}$(CH$_2$)$_{n7}$(CH=CH)$_{n8}$(CH$_2$)$_{n9}$—. The sum of n1+2n2+n3+2n4+n5+2n6+n7+2n8+n9 is an integer of from 1 to 21, with each of n2, n4, n6 and n8 being independently zero or 1. n1 is equal to zero or an integer of from 1 to 21, n3 is equal to zero or an integer of from 1 to 18, n5 is equal to zero or an integer of from 1 to 15, n7 is equal to zero or an integer of from 1 to 12, n9 is equal to zero or an integer of from 1 to 9, and each of n1 to n9 can be the same or different at each occurrence. $Y^2$ is —CH$_3$, —CO$_2$H or —CH$_2$OH.

$X^1$ is a hydrolysis promoting group ("HPG") including, but not limited to: F, Cl, Br, I, the group —OC$_6$H$_4$X$^2$ or the group —C(O)X$^2$, wherein X$^2$ is F, Cl, Br, I, NH$_3^+$, NO$_2$ or CN. Most preferably, X$^1$ is F, Cl, Br or I. The X$^1$ in CHX$^1$ could have (R) or (S) configuration or could be a mixture of (R) and (S) configurations. Preferably, $A^1$ is the group Z—C(O)NHCH(C$_6$H$_5$)CH(OR)C(O)—; Z is preferably C$_6$H$_5$ and $A^1$ is more preferably the group C$_6$H$_5$C(O)NHCH(C$_6$H$_5$)CH(OR)C(O)—. Most preferably, $A^1$ is C$_6$H$_5$C(O)NHCH(C$_6$H$_5$)CH(OR)C(O)—, $A^2$ is CH$_3$C(O)— and $A^3$ is H, that is, the taxane is a paclitaxel. When $R^1$ is a hydrogen, R is then —Y$^1$Y$^2$, and when R is a hydrogen, $R^1$ is —Y$^1$Y$^2$. The group —Y$^1$Y$^2$ preferably has the formula —Y$^1$CH$_3$, more preferably, the formula —C(O)CHX$^1$(CH$_2$)$_{n1}$CH$_3$; still more preferably, n1 is then 3, 5, 9, 11, 13 or 15.

Taxanes with α-substituted carbonyl compounds esterified to the 2' or 7 hydroxy position have therapeutic activity. "Hydrolysis-promoting groups" (HPG) that facilitate chemical hydrolysis by means of a redistribution of electronic density may be important in conversion of substituted taxanes to paclitaxel or other therapeutic taxanes. This conversion may also be important to their biological activity. However, the substituted taxane may itself have biological activity without being converted to the parent compound.

The biological activity of paclitaxel is known to be sensitive to the chirality of paclitaxel chemical moieties and therefore, the stereochemistry of α-substituted carbonyl compounds esterified to the 2' or 7 hydroxy position of taxanes may be important to the biological activity of the compound.

Ester cleavage of α-substituted carbonyl compounds has been shown to be selective for a single enantiomer for many enzymes ("Lipases for Resolution and Asymmetric Synthesis" Amano Enzymes USA Co. Lombard, Ill., December 1998.). Although chemical hydrolysis of taxanes with α-substituted carbonyl compounds esterified at the 2' or 7 hydroxy position due to HPG is not stereoselective, biologically mediated cleavage could be stereospecific, as judged by the selectivity of many enzymes. The stereospecific cleavage of α-substituted carbonyl compounds esterified to the 2' or 7 hydroxy position of taxanes could be a factor affecting conversion of the pro-drug. Thus, the chirality of the linkage at the α-substituted carbonyl group may have pharmacological implications.

Thus, in one embodiment, the invention provides hydrophobic taxane compositions having a preponderance of (S) or (R) α-substituted carbonyl groups, preferably α-substituted fatty acids, for instance, (S) and (R) 2-bromohexadecanoic acids substituted at the 2' or 7 hydroxy position. Methods for preparing these single enantiomers and for separating them from an enantiomeric mixture is also provided.

Also provided herein are compositions comprising the taxane of this invention. Such compositions can also comprise a pharmaceutically acceptable medium may be selected from the group consisting of a polyoxyethylated derivative of castor oil, polysorbate (Tween) 80, dimethyl sulfoxide, carboxymethyl cellulose, hydroxypropylcellulose, polyethylene glycols (PEGs) including PEG-400 and PEG-hydroxystearate, triacetin, soybean oil, lecithin and soy lipids or combinations thereof. Preferably, the pharmaceutically acceptable medium is a polyoxyethylated derivative of castor oil. More preferably, the pharmaceutically acceptable medium is USP/NF Polyoxyl 35 Castor Oil. Most preferably, the pharmaceutically acceptable medium is Cremophor-ELP®. The pharmaceutically acceptable medium may also be a lipid carrier and may be any composition which maintains the chemical integrity of the HPG containing taxane throughout an acceptable pharmaceutical shelf life, effectively delivers the derivatized taxane of this invention to an animal in need of such treatment wherein the side effects due to the carrier are within acceptable medical limits. The compositions may comprise a lipid-based carrier, e.g., a fatty acid, phospholipid, lipoprotein, micelle, lipid complex or liposome, with which the taxane is associated so as to deliver the taxane to a site in the body where it can be therapeutically effective.

The lipid carrier may be a liposome or non-liposomal lipid carrier. If the lipid carrier is a liposome, it is most preferably, a multilamellar liposome. The liposome preferably comprises a lipid component which comprises a saturated lipid, more preferably, a saturated phosphatidylcholine such as dimyristoyl phosphatidylcholine, dipalmitoyl phosphatidylcholine or distearoyl phosphatidylcholine. Most preferably, the saturated lipid is dimyristoyl phosphatidylcholine. The liposomal lipid component can consist essentially of a saturated lipid, e.g., dimyristoyl phosphatidylcholine. For taxanes associated with lipid carriers, the sum of n1+2n2+n3+2n4+n5+2n6+n7+2n8+n9 is preferably an integer of from 3 to 21, more preferably an integer of from 9 to 21, and most preferably, an integer of from 13 to 21. That is, in compositions comprising taxanes associated with liposomal lipid carriers, the carrier has a lipid component comprising or consisting essentially of dimyristoyl phosphatidylcholine and the taxane is derivatized with α-substituted carbonyl compound. If the carrier is not a liposome, then preferably, it is the polyoxyethylated derivative of castor oil (USP/NF Polyoxyl 35 Castor Oil).

Further provided herein is a method of administering a taxane to an animal, which comprises administering a taxane-containing composition of this invention to the animal. Preferably, the taxane thus administered is associated in the composition with a lipid carrier, more preferably, a liposome or the polyoxyethylated derivative of castor oil (USP/NF Polyoxyl 35 Castor Oil) and most preferably, if a liposome, a multilamellar liposome and if a non-liposomal carrier, then the polyoxyethylated derivative of castor oil (USP/NF Polyoxyl 35 Castor Oil). The animal can be afflicted with a cancer, e.g., a brain, stomach, lung, colon, prostate, breast or ovarian cancer, cancers of the head and neck, or a leukemia, lymphoma, carcinoma or sarcoma. The compounds of the present invention may also be administered to an animal afflicted with inflammatory diseases such as arthritis. (Arsenalt, A. L., et al. (1998) Clin Immunol Immunopathol, 86(3):280–9.) Cancer treatment by this method involves administering an anticancer effective amount of a taxane to the affected animal. Typically, this anticancer effective amount of the taxane is from about 0.1 mg per kg of body weight of the animal to about 1000 mg per kg. For such anticancer treatment, the composition administered preferably contains a lipid carrier. Preferred anticancer taxanes are paclitaxels, i.e., taxanes wherein $A^1$ is $C_6H_5C(O)NHCH(C_6H_5)CH(OR)C(O)-$, $A^2$ is $CH_3C(O)-$ and $A^3$ is H. More preferably, R or $R^1$ is $-C(O)CHX^1(CH_2)_{n1}CH_3$, and most preferably, n1 is then 3, 5, 9, 11, 13 or 15. Further provided are taxane derivatives wherein the $X^1$ in $CHX^1$ could have either (R) or (S) configuration or could be a mixture of (R) and (S) configurations. Furthermore, an additional bioactive agent can be administered to an animal as part of administration of a taxane to the animal.

Other and further objects, features and advantages will be apparent from the following description of the preferred embodiments of the invention given for the purpose of disclosure when taken in conjunction with the following drawings.

BRIEF DESCRIPTION OF THE DRAWING

FIG. 1. Effect of Paclitaxel- and 2'-(2-Bromoacyl) Hydrophobic Paclitaxel Derivative ("HTD")-Containing Liposomes on the Survival of OVCAR-3 Tumor-Bearing SCID Mice. Filled diamonds: paclitaxel liposomes; filled squares: 2-bromo-C6 HTD (paclitaxel substituted with a 6-carbon acyl chain attached to paclitaxel's 2' hydroxyl group, the acyl chain having a bromine atom attached to its alpha carbon); filled triangles: 2'-(2-bromocapryanoyl) paclitaxel (2-bromo-C8 HTD): open diamonds: 2'-(2 bromolauranoyl) paclitaxel (2-bromo-C12 HTD); open triangles: 2'-(2 bromomyrstanoyl) paclitaxel (2-bromo-C14 HTD); open circles:: 2'-(2 bromopalmitanoyl) paclitaxel (2-bromo-C16 HTD); and, *: "empty" liposomes (liposomes not containing paclitaxel or a substituted paclitaxel derivative).

FIG. 4. CD spectrum of 2-bromohexadecanoyl methyl ester prior to (solid line) and following (doffed line) enzymatic cleavage.

DETAILED DESCRIPTION OF THE INVENTION

Figure 2A:
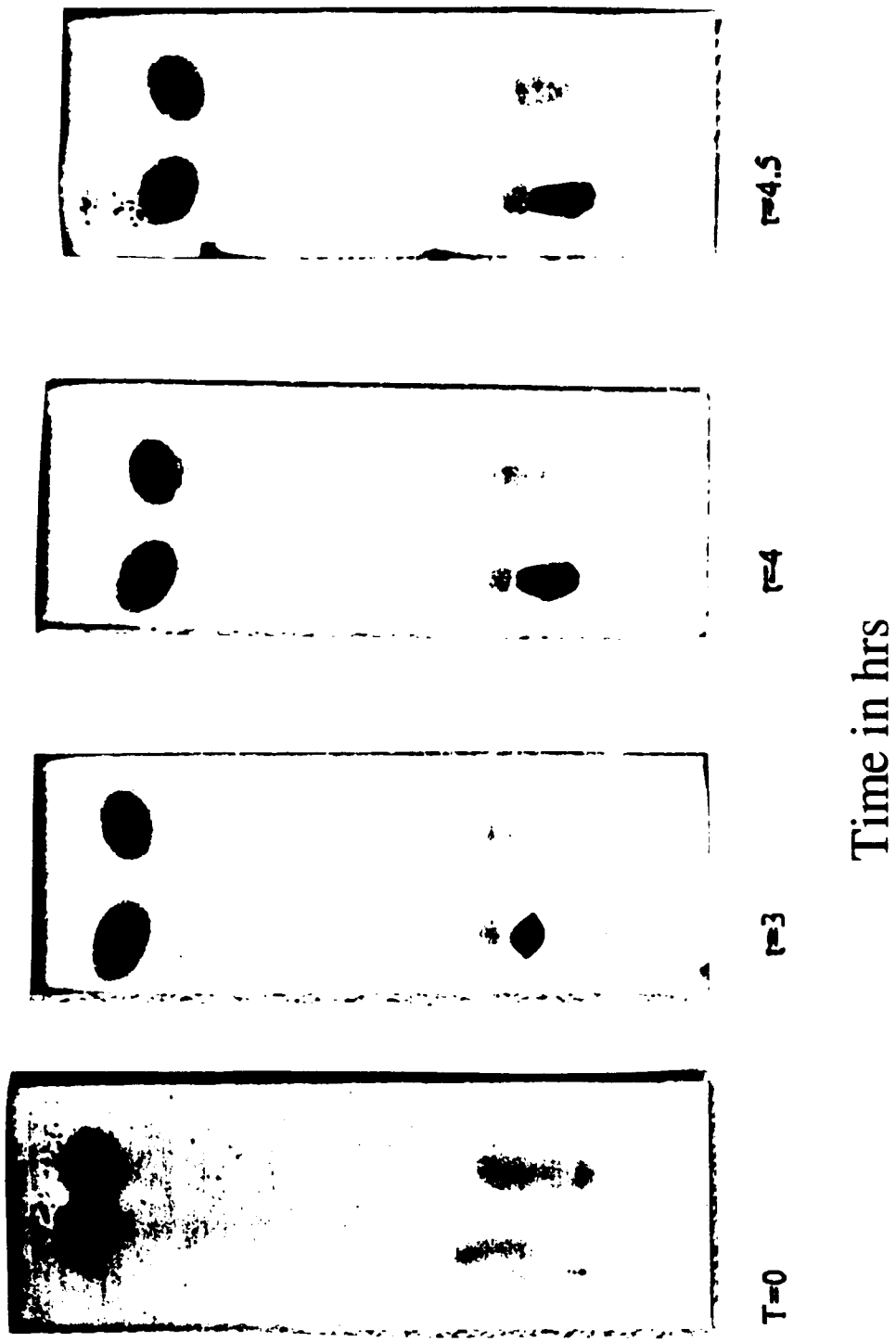
FIG. 2. The time course of enzymatic cleavage of (±)-2-bromohexadecanoyl methyl ester with lipase from *Pseudomonas cepacacia,* and monitored by thin layer chromatography.

This invention provides a taxane having the formula:

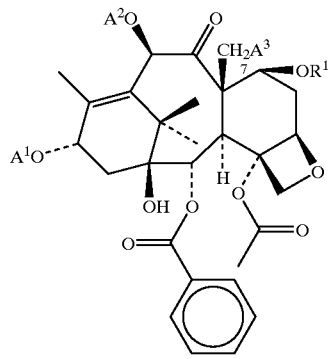

$A^1$ is H or a group having the formula $Z-C(O)NHCH(C_6H_5)CH(OR)C(O)-$, $A^2$ is H or $CH_3C(O)-$, and $A^3$ is H or OH. Z is $C_6H_5$, $C_6H_5CH_2-O-$, $C(CH_3)_3-O-$ or $CH(CH_3)=C(CH_3)-$. Most preferably, $A^1$ is $C_6H_5C(O)NHCH(C_6H_5)CH(OR)C(O)-$, $A^2$ is $CH_3C(O)-$ and $A^3$ is H. Each of R and $R^1$ is H or a group having the formula $Y^1Y^2$, provided that at least one of R and $R^1$ is not H, $Y^1$ is a group having the formula $-C(O)CHX^1(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}-$. The sum of n1+2n2+n3+2n4+n5+2n6+n7+2n8+n9 is an integer of from 1 to 21, with each of n2, n4, n6 and n8 being independently zero or 1. n1 is equal to zero or an integer of from 1 to 21, n3 is equal to zero or an integer of from 1 to 18, n5 is equal to zero or an integer of from 1 to 15, n7 is equal to zero or an integer of from 1 to 12, n9 is equal to zero or an integer of from 1 to 9, and each of n1 to n9 can be the same or different at each occurrence. $Y^2$ is $-CH_3$, $-CO_2H$ or $-CH_2OH$.

$X^1$ is a hydrolysis promoting group ("HPG") selected from the group consisting of F, Cl, Br, I, the group $-OC_6H_4X^2$ and the group $-C(O)X^2$, wherein $X^2$ is F, Cl, Br, I, $NH_3^+$, $NO_2$ or CN. In one embodiment the $X^1$ in $CHX^1$ is stereospecifically attached to the α carbonyl group; preferably the HPG could have (R) or (S) configuration or could be a mixture of (R) and (S) configurations. Preferably, $A^1$ is the group $Z-C(O)NHCH(C_6H_5)CH(OR)C(O)-$; Z is preferably $C_6H_5$ and $A^1$ is more preferably the group $C_6H_5C(O)NHCH(C_6H_5)CH(OR)C(O)$—. Most preferably, $A^1$ is $C_6H_5C(O)NHCH(C_6H_5)CH(OR)C(O)$—, $A^2$ is $CH_3C(O)$— and $A^3$ is H, that is, the taxane is paclitaxel. When $R^1$ is a hydrogen, R is then —$Y^1Y^2$, and when R is a hydrogen, $R^1$ is —$Y^1Y^2$. The group —$Y^1Y^2$ preferably has the formula —$Y^1CH_3$, more preferably, the formula —$C(O)CHX^1(CH_2)_{n1}CH_3$; still more preferably, n1 is then 3, 5, 9, 11, 13 or 15.

The taxane most preferred herein is a paclitaxel ([Compound I]; TAXOL® ($C_{47}H_{51}NO$), Bristol-Myers Squibb) derivative.

However, taxotere (II)-based derivatives, which differ from paclitaxel by having a tert-butoxy carbonyl group at the C-12 position, instead of a benzoyl group, and a hydroxyl group, instead of an acetyloxy group, at C-10 are also provided herein. Accordingly, for taxotere, $A^1$ is $C(CH_3)_3OC(O)NHCH(C_6H_5)CH(OR)C(O)$—, $A^2$ is H, and $A^3$ is H.

Further taxanes useful in accordance with the practice of this invention are known in the art and include, without limitation: Cephalomannine (III); 19-hydroxybaccatin III [IV], (McLaughin et al., *J. Nat. Prod.*, Vol. 44:312–319 (1981)) Baccatin V [V], 10-deacetyl cephalomannine [VI], 10-deacetyl paclitaxel [VII], 7-Epi-10-deacetyl paclitaxel [VIII], 7-Epi-10-deacetyl cephalomannine [IX], and 10-deacetyl baccatin III [X], as described in the following table.

| Compound | $A^1$ | $A^2$ | $A^3$ |
| --- | --- | --- | --- |
| Paclitaxel (I) | $C_6H_5C(O)NHCH(C_6H_5)CH(OR)C(O)$— | $CH_3C(O)$— | H |
| Taxotere (II) | $C(CH_3)_3OC(O)NHCH(C_6H_5)CH(OR)C(O)$— | H | H |
| Cephalomannine (III) | $(CH_3)CH=C(CH_3)C(O)NHCH(C_6H_5)CH(OR)C(O)$— | $CH_3C(O)$— | H |
| 19-hydroxy baccatin III (IV) | H | $CH_3C(O)$— | OH |
| Baccatin III (V) | H | $CH_3C(O)$— | H |
| 10-Deacetyl cephalo mannine (VI) | $(CH_3)CH=C(CH_3)C(O)NHCH(C_6H_5)CH(OR)C(O)$— | H | H |
| 10-Deacetyl taxol (VII) (7α-OH) | $C_6H_5C(O)NHCH(C_6H_5)CH(OR)C(O)$— | H | H |
| 7-Epi-10-deacetyl taxol(7β-OH) (VIII) | $C_6H_5C(O)NHCH(C_6H_5)CH(OR)C(O)$— | H | H |
| 7-Epi-10-deacetyl cephalo mannine(7β-OH) (IX) | $(CH_3)CH=C(CH_3)C(O)NHCH(C_6H_5)CH(OR)C(O)$— | H | H |
| 10-Deacetyl baccatin III (X) | H | H | H |

Each of R and $R^1$ is H or a group having the formula —$Y^1Y^2$, provided that at least one of R and $R^1$ is not H and provided that when $A^3$ is H, $R^1$ is not H. $Y^1$ is the group —$C(O)CHX^1(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}$—. The sum of n1+2n2+n3+2n4+n5+2n6+n7+2n8+n9 is an integer of from 1 to 21, wherein each of n2, n4, n6 and n8 is independently zero or 1. n1 is equal to zero or an integer of from 1 to 21, n3 is equal to zero or an integer of from 1 to 18, n5 is equal to zero or an integer of from 1 to 15, n7 is equal to zero or an integer of from 1 to 12, and n9 is equal to zero or an integer of from 1 to 9. Each of n1 to n9 can be the same or different at each occurrence. Preferably, $Y^1$ is saturated, that is, there are no double bonds between adjacent carbon atoms. Accordingly, n2, n4, n6 and n8 are each preferably zero, n3, n5, n7 and n9 are each also zero, and $Y^1$ is preferably —$C(O)CHX^1(CH_2)_{n1}$—. Alternatively, $Y^1$ can be unsaturated, that is, it can have one or more double bonds and one or more CH=CH units; accordingly, at least one of n2, n4, n6 and n8 is then 1. For example, when the unsaturated acyl chain has one double bond: n2 is 1, n4, n6 and n8 each being zero; $Y^1$ is then —$C(O)CHX^1(CH_2)_{n1}CH=CH(CH_2)_{n3}$—; n1 is zero or an integer from 1 to 18; n3 is also zero or an integer from 1 to 18, at least one of n1 or n3 is not zero, and the sum of n1 plus n3 is equal to an integer of from 1 to 19. The $X^1$ in $CHX^1$ could have either (R) or (S) configuration or could be a mixture of (R) and (S) configurations. The mixture may have greater than 0% of either enantiomer and less than 100% of the other enantiomer or any other ratio of the two enantiomeric forms.

$Y^2$ is preferably —$CH_3$, the acyl chain thus being derived from a monocarboxylic acid, but can also be —$CO_2H$, the acyl chain being derived from an omega dicarboxylic acid, or —$CH_2OH$, the acyl chain then being derived from an omega hydroxy acid. Accordingly, the group $Y^1Y^2$ preferably has the formula —$C(O)CHX^1(CH_2)_{n1}CH_3$, wherein n1 is most preferably equal to 3, 5, 9, 11 or 13, whether the group be located at R, $R^1$ or both R and $R^1$.

"Attachment" of the group —$Y^1Y^2$ to a taxane means forming a chemical connection between the group and the taxane by any means generally accepted in the art for forming such connections. Attachment is to one or more reactive groups, typically hydroxy groups, on the taxane. Attachment of any acyl chain to a taxane can stabilize the taxane-lipid carrier association, such that the taxane and carrier remain together, for example, in the plasma of animals for a longer period of time than does the corresponding acyl chain-free taxane. Increased stability of association enhances the amount of the taxane reaching its intended site of therapeutic action in vivo.

Paclitaxel, for example, has three hydroxyl groups to which acyl chains can be attached; these are located at the 1, 2' and 7 positions, with their relative order of reactivity generally believed to be (from most reactive to least reactive) 2'>7>1. Hydrocarbons can be attached to the primary reactive group of a taxane. Alternatively, acyl chains (—$Y^1Y^2$) containing HPG can be substituted for the A2, acetate or benzoyloxy moieties of the taxane ring.

For example, the 2' OH group of paclitaxel, utilizing stoichiometric amounts of an active form of the acid, e.g., chlorides or anhydrides. The hydroxyl group at the 7 position of paclitaxel can be modified by attaching an acyl chain to both the 2' and 7 OH groups, and then selectively removing the 2' acyl chain so that the acyl chain at the 7 position remains attached to paclitaxel. Selective removal of the 2' acyl chain can be accomplished using stoichiometric amounts of a mild base, e.g., sodium bicarbonate. Additionally, the 7 OH group of paclitaxel can be modified by "protecting" the 2' OH group before covalently linking paclitaxel with the acyl chain. The 2' OH group can also be protected with groups such as, for example, triphenyl methyl, methoxytriphenyl methyl, trifluoroacetyl and TrOC (trichloromethoxy chloroformate) groups, using processes generally known to ordinarily skilled artisans. The protected paclitaxel is then reacted with an active form of the acyl chain, e.g., anhydrides or chlorides, in anhydrous organic solvent, and bases such as DMAP and pyridine. The protecting group can be removed from the 2' position by well known and readily practiced means, under mildly acidic or basic conditions; TrOC groups, for example, can be removed by zinc reduction reactions. Reactions are typically performed in the presence of a base, such as pyridine, dimethylaminopyridine ("DMAP"), triethylamine, or others, and in common polar, aprotic organic solvents such as dimethyl formamide, dimethyl sulfoxide and the like. The progress of the reaction can be monitored by a number of well known chromatographic means, for example, thin layer chromatography using a 3% methanol-in-chloroform solvent system. The compound's identity can be confirmed by spectroscopic procedures, such as NMR spectroscopy.

For example, the following reaction scheme, and the information described below, can be used to prepare 2'-[(±)-2-Bromoacyl] paclitaxels:

reacted with a stereospecific enzyme to cleave the methyl group, forming a mixture of one steroisomer of the 2-bromo fatty acid and the methyl ester of the other isomer. The two compounds may be separated using common separation techniques such as chromatography, yielding the enantiomerically pure or a mixture with an excess of one enantiomer. To obtain the other HPG containing isomer, the separated methyl ester may then be converted to the carboxylic acid by chemical means. Ether isomer (R') may then be reacted with the taxane to form a taxane with an α substituted carbonyl containing compound.

However, specific reaction and purification conditions are generally expected to vary according to a number of factors, including without limitation, the raw materials and reactants used, that are well within the purview of ordinarily skilled artisans to determine and control given the teachings of this invention.

Acyl chains substituted with a hydrolysis-promoting group on the alpha carbon can be purchased from commercially available sources, or synthesized according to any of the means generally accepted in the art for substitution of a

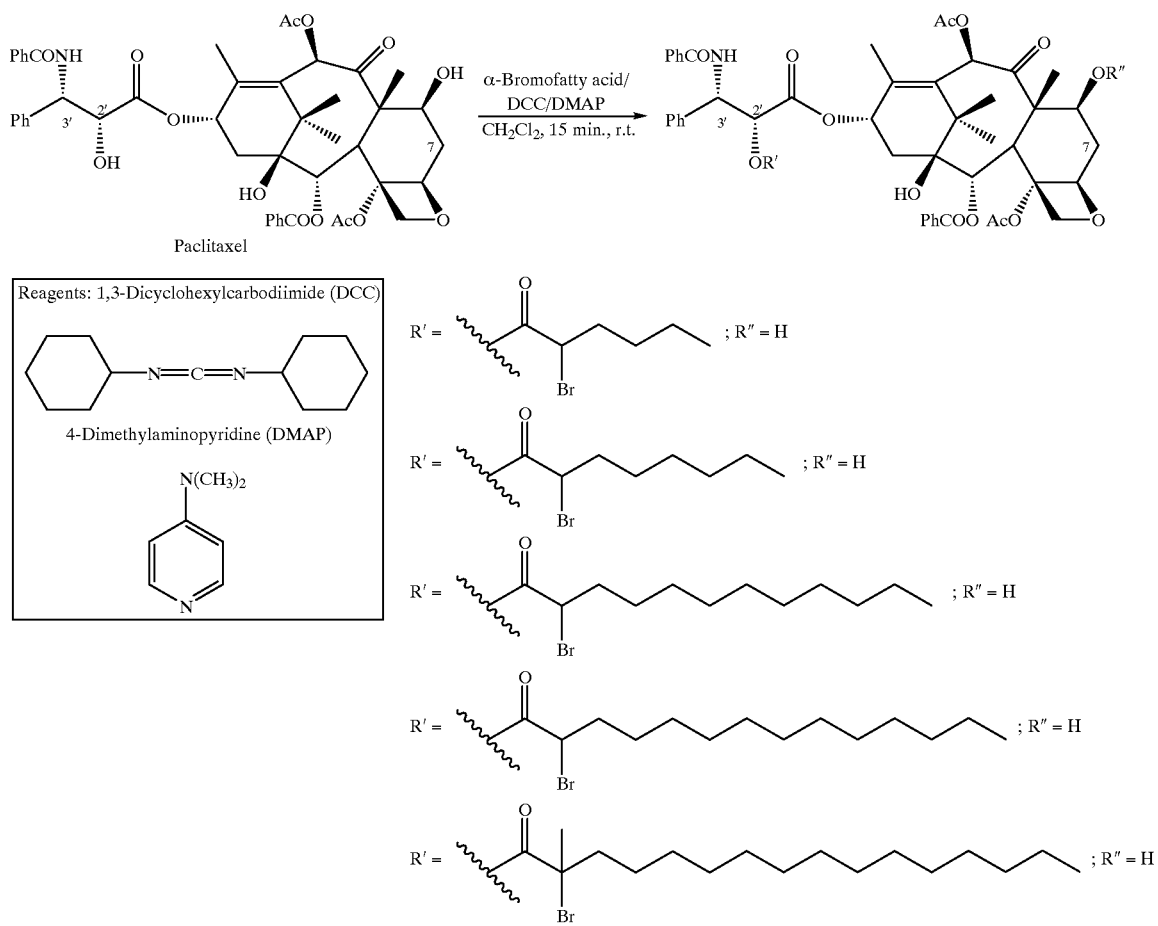

Alternatively, preparation of paclitaxel derivatives having acyl derivatives of enhanced or pure enantiomeric forms can be accomplished by using enantiomerically pure R' or mixtures enriched in one enantiomeric configuration instead of racemic mixtures of R'.

An example of a procedure for obtaining an α-substituted carbonyl containing compound with an enantiomeric excess of one enantiomer follows: the racemic mixture of the 2-bromo fatty acid may be methylated, and subsequently hydrogen atom on the alpha carbon of a fatty acid. Single enantiomeric forms of the fatty acids are not commercially available. Thus, the present invention provides a method to prepare acyl chains enriched in a single enantiomeric form at the alpha carbon.

"Hydrolysis-promoting-groups" ("HPGs") are substitutions at a carbonyl group's alpha carbon (Cα) that promote hydrolysis of the bonds between a parent taxanes its attached carbonyl group. Preferably, the carbonyl group is an acyl chain. The HPGs are electronegative relative to hydrogen, meaning that they draw electrons to themselves more than a hydrogen atom would if it occupied the same position in the same molecule. Accordingly, substitution of a hydrolysis-promoting group for a hydrogen atom on the alpha carbon results in a redistribution of, for instance, an acyl chain's electron density, and thereby causes an inductive effect in the acyl chain. Substitution of an aromatic moiety-containing HPGs for alpha carbon-attached hydrogens can also cause resonance effects, these too involving electron density redistribution in the substituted acyl chain. HPG-induced induction and resonance effects stabilize an acid's corresponding base form, but not the acid itself, and thereby causes the acid to be a stronger acid than it would be if there was a $CH_2$ group in the acyl chain instead of the HPG. HPG-substituted acyl chains thus generally have lower $pK_\alpha$'s than their corresponding native forms, that is, the form in which a $CH_2$ group is present at the alpha position instead of an HPG-substituted group, and hence, HPG-substituted carbonyl groups, for instance, acyl chains are more readily hydrolyzable from their parent taxanes than are nonsubstituted chains. Accordingly, the hydrolysis-promoting group $X^1$ can be any atom or group of atoms: (1) having an electronegativity greater than hydrogen; and, (2) that can be attached at the alpha position of an acyl chain. $X^1$ can, for example, be F, Cl, Br, I, $NH_3^+$, the group $—OC_6H_4X^2$ or the group $—C(O)X^2$; $X^2$ is, for example, F, Cl, Br, I, $NH_3^+$, $NO_2$ or CN. Preferably, $X^1$ is F, Cl, Br or I. The $X^1$ in $CHX^1$ could have (R) or (S) configuration or could be a mixture of (R) and (S) configurations.

The substitution on the alpha carbon of the acyl chain attached to the taxane may be a single enantiomer or a mixture of enantiomeric forms. The mixture may contain from greater than (0)% to less than 100% of one enantiomeric form, for instance, the mixture may contain 10% of the (S) form and 90% of the (R) form. The term single enantiomeric form means a composition that is substantially enriched in one of the enantiomeric forms. It need not contain 100% of a single enantiomeric form.

Also provided herein is a composition comprising a taxane of this invention. Compositions intended for therapeutic use of the taxane preferably comprise a pharmaceutically acceptable medium, which is a medium generally intended for use in connection with the administration of active ingredients, such as therapeutic or diagnostic agents, to animals. These include, without limitation: solids, such as pills, capsules and tablets; gels; excipients; and aqueous or nonaqueous solutions.

Pharmaceutically acceptable media are generally formulated according to a number of factors well within the purview of the ordinarily skilled artisan to determine and account for, including without limitation: the particular active ingredient used, its concentration, stability and intended bioavailability; the disease, disorder or condition being treated with the composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, J. G. Nairn, in: *Remington's Pharmaceutical Science* (A. Gennaro, ed.), Mack Publishing Co., Easton, Pa., (1985), pp. 1492–1517, the contents of which are incorporated herein by reference). Typical pharmaceutically acceptable media used in parenteral drug administration include, for example, D5W, an aqueous solution containing 5% weight by volume of dextrose, and physiological saline. A polyoxyethylated derivative of castor oil (USP/NF Polyoxyl 35 Castor Oil) may also be used to administer the hydrolyzable hydrophobic taxanes of the present invention.

Taxane-containing pharmaceutical compositions provided herein preferably comprise a lipid carrier with which the taxane is associated. "Lipid carriers" are hydrophobic or amphipathic molecules suitable for administration to animals, and include, without limitation: fatty acids, phospholipids, micelles, lipoproteins, lipid complexes, i.e., nonliposomal, lipid-based structures which may, but are not required to contain one or more nonlipid components, and liposomes. Preferably, the lipid carrier is a liposome or a polyoxyethylated derivative of castor oil (USP/NF Polyoxyl 35 Castor Oil).

Cremophor EL® is an excipient reported to have undesirable side effects (Straubinger (1995) Taxol; Science and Applications, ed. M. Suffness, CRC Press, Boca Raton). Thus, the administration of as little of this excipient as possible can be accomplished by providing a taxane derivative having greater solubility in the excipient than does paclitaxel. The hydrophobic taxane provides this advantage.

The Cremophor EL®:ethanol (1:1) formulation used to formulate paclitaxel as Taxol® is not optimal for taxanes containing α substituted carbonyl containing moieties that promote hydrolysis. Nucleophilic solvents such as ethanol and water react with the HPG containing taxanes resulting in the release of the HPG moiety from the taxane. Although the hydrolysis may be important biologically, prior to administration, hydrolysis during storage may limit the shelf life of the drug and affect its efficacy as a therapeutic agent. Thus, it is preferable to store the taxane derivative in a medium that contains as little as possible of nucleophilic solvents. Preferably, the storage medium contains less than 10% of these solvents during storage; more preferably the storage medium is a polyoxyethylated derivative of castor oil; and most preferably the storage medium is Cremophor® ELP (BASF product number 205104). Cremophor® ELP meets the specifications for USP/NF Polyoxyl 35 caster oil. However, Cremophor® ELP has additional specifications limiting the amount of ethylene oxide, 1,4-dioxane, potassium, free fatty acids, and ricinoleic, oleic and palmitic acids. In addition, the pH of Cremophor® ELP is 5–7, while the pH of Cremophor® EL is 6–8. The more stringent specifications of Cremophor® ELP may decrease the side effects of the cremophor and may decrease the degradation of the HTD (hydrolyzable taxane derivatives) during storage. Other excipients may also be suitable for obtaining the same long term storage and decrease in side effects as Cremophor® ELP. A formulation of one preferred embodiment of the present invention, 2'-(R)-[2-bromohexadecanoyl] paclitaxel with Cremophor® ELP at a drug to Cremophor® ELP ratio of 30:1 on a weight ratio, 2.5 times greater than the weight ratio of the Taxol® formulation.

"Liposomes" comprise one or more bilayers of lipid molecules, each bilayer encompassing an aqueous compartment. Unilamellar liposomes have a single lipid bilayer, and multilamellar liposomes have more than one bilayer. The amphipathic lipid molecules which make up lipid bilayers comprise a polar (hydrophilic) headgroup and one or two acyl chains. The polar groups can be phosphate-, sulfate- or nitrogen-based groups, but are preferably phosphate groups, such as phosphorylcholine, phosphorylethanolamine, phosphorylserine, phosphorylglycerol or phosphorylinositol groups. The acyl chains generally comprise from 12 to 24 carbon atoms, and can be saturated (e.g., lauric, myristic, palmitic, or stearic acid), or unsaturated (e.g., oleic, linoleic, linolenic, or arachidonic acid). Liposomal lipid can also include sterols, such as cholesterol, and other lipids.

Liposomes can be made by a variety of methods, including: Bangham's methods for making multilamellar liposomes (MLVs) involving drying of a lipid/organic solvent solution and then rehydrating the dried lipids with an aqueous solution (see Bangham et al., 1965); Lenk's, method for making MLVs with substantially equal interlamellar solute distribution (SPLVs) involving forming a biphasic mixture of an aqueous phase and a lipid-containing organic phase, and then emulsifying the lipid in the aqueous phase while evaporating the organic (see U.S. Pat. Nos. 4,522,803, 5,030,453, and 5,169,637); Fountain's (U.S. Pat. No. 4,588,578) method of making SPLVs using a monophasic solvent system; Cullis' (U.S. Pat. No. 5,008,050) method of making SPLVs using repeated cycles of freezing and thawing; preparation of REVs through formation of a water-in-oil emulsion, from which the organic phase is evaporated to give a gel, the gel then being agitated to give oligolamellar liposomes (see Papahadjopoulos et al., U.S. Pat. No. 4,235,871); extrusion of MLVs to make unilamellar liposomes (see, e.g., Cullis et al., U.S. Pat. No. 4,975,282); as well as sonication or homogenization of larger liposomes, or ether or ethanol injection processes (see, for example, R. Deamer and P. Uster, "Liposome Preparation: Methods and Mechanisms," in *Liposomes* (M. Ostro, ed.), Marcel Dekker, Inc., New York (1983), pp. 27–52). The contents of these liposome preparation documents are incorporated herein by reference.

More preferably, the liposome is a multilamellar liposome. The liposome preferably has a lipid component which comprises a saturated lipid; the lipid component can consist essentially of the saturated lipid. The saturated lipid is preferably a phosphatidylcholine such as dimyristoyl phosphatidylcholine, dipalmitoyl phosphatidylcholine and distearoyl phosphatidylcholine. More preferably, the phosphatidylcholine is dimyristoyl phosphatidylcholine. Taxanes associated with lipid carriers in pharmaceutical compositions preferably have an acyl chain which is at least six carbon atoms long, more preferably at least twelve carbon atoms long, and most preferably, at least 16 carbon atoms long; the acyl chain is preferably saturated.

High sensitivity differential scanning calorimetry (DSC) was used to examine the effect of addition of taxol and its acylated derivatives on the thermotropic phase properties of phosphocholine bilayers of saturated 1,2-dimyristoyl-sn-glycero-3-phosphocholines (DMPC), 1,2-dipalmitoyl-sn-glycero-3-phosphocholines (DPPC), and 1,2-distearoyl-sn-glycero-3-phosphocholines (DSPC). Likewise, three acylated taxol prodrugs were varied in chain lengths from six, twelve, to sixteen carbons. The DSC data showed that taxol had little or no effect on the perturbation of all three PC bilayers as high as 9.1 mol % (Lipid/Drug, 10:1). In contrast, the addition of prodrugs into short-chain DMPC and DPPC bilayers, for instance, caused a significant perturbation as observed by the disappearance of pretransitions and broadening in the main phase transition temperatures ($T_m$) of both PCs. However, the perturbation was much significant with the long acyl chains, suggesting the intercalation of the prodrugs acyl chain into the bilayers. The long-chain DSPC bilayers, on the other hand, showed less significant change in the DSC profile at any mol % of prodrugs but indeed show some degree of association with the bilayers.

The lipid carrier of the present invention is preferably a polyoxyethylated derivative of castor oil (USP/NF Polyoxyl 35 Castor Oil). and the taxane is derivatized with a sixteen carbon-long saturated acyl chain having a bromine atom at the alpha carbon. Alternatively, the lipid carrier may be a multilamellar liposome having a lipid component which comprises or consists essentially of dimyristoyl phosphatidylcholine.

"Association" as used herein generally means association between the acyl chain attached to the taxane and the hydrophobic portion of the lipid carrier. Without intending to be limited by theory, it is believed that such association is by way of a number of influences, such as Van der Waal's forces, generally known to operate between hydrophobic molecules in an aqueous environment. Means of determining the stability of such associations, for example, by determining the percentage of taxane recoverable with phosphorous when the lipid carrier comprises a phospholipid are readily practiced by ordinarily skilled artisans given the teachings of this invention.

Lipid carriers associated with the taxane of this invention can comprise an additional bioactive agent, that is, a bioactive agent in addition to the taxane. Lipid carrier/bioactive agent formulations can enhance the therapeutic index of the bioactive agent, for example by buffering the agent's toxicity and by reducing the rate at which the agent is cleared from the circulation of animals, thereby meaning that less of the agent need be administered to achieve the desired therapeutic effect. "Bioactive agents" are compounds or compositions of matter having biological activity on animal cells in vitro or when administered to an animal; bioactive agents can have therapeutic and/or diagnostic activity. Such agents include, but are not limited to, antimicrobial, anti-inflammatory and anticancer agents as well as radioactive isotopes, enzymes and dyes. Additional bioactive agents also include bioactive lipids, such as certain ceramides and ether lipids, which themselves have therapeutically beneficial properties. Preferably, the additional bioactive agent is an anticancer agent.

Lipid carriers can also comprise one or more "headgroup-modified lipids." These comprise polar groups derivatized by attachment thereto of a moiety which can inhibit the binding of serum proteins to headgroup-modified lipid-containing lipid carriers. This alters the pharmacokinetic behavior of the carriers such that they remain in circulation longer (see, e.g., Blume et al., Biochim. Biophys. Acta. 1149:180 (1993); Gabizon et al., Pharm. Res. 10(5):703 (1993); Park et al. Biochim. Biophys Acta. 1108:257 (1992); Woodle et al., U.S. Pat. No. 5,013,556; Allen et al., U.S. Pat. Nos. 4,837,028 and 4,920,016; the contents of these documents being incorporated herein by reference).

Headgroup-modified lipids are typically phosphatidylethanolamines (PE's), for example dipalmitoyl phosphatidylethanolamine ("DPPE"), palmitoyloleoyl phosphatidylethanolamine ("POPE") and dioleoyl phosphatidylethanolamine ("DOPE"), amongst others. Such lipids have headgroups generally derivatized with organic dicarboxylic acids, such as succinic or glutaric acid ("GA"), or their corresponding anhydrides.

The amount of the headgroup-modified lipid incorporated into the lipid carrier generally depends upon a number of factors well known to the ordinarily skilled artisan, or within his purview to determine without undue experimentation. These include, but are not limited to: the type of lipid and the type of headgroup modification; the type and size of the carrier; and the intended therapeutic use of the formulation. Typically, from about 5 mole percent to about 20 mole percent of the lipid in a headgroup-modified lipid-containing lipid carrier is headgroup-modified lipid.

Further provided herein is a method of administering a taxane to an animal, which comprises administering the composition of this invention to the animal, preferably a mammal such as a human. Administration is by any means generally accepted for administration of therapeutic agents to animals, but is preferably intravenous or intraperitoneal.

Animals afflicted with cancers can be treated by therapeutic administration of taxane-containing compositions, wherein the compositions comprise an anticancer or anti-inflammatory effective amount of a taxane.

Generally, those cancers treatable by this method are those which are, or may be, treated with the corresponding free taxane, i.e., a taxane not having an attached acyl chain. These include, without limitation: brain, breast, colon, lung, ovarian, prostate, pancreatic and stomach cancers, cancers of the head and neck; as well as, leukemias, lymphomas, sarcomas and carcinomas. The cancer treated can be a cancer that is resistant to standard therapeutic regimens, i.e., a drug-resistant cancer. In addition, certain inflammatory conditions may be treatable by the compound of the present invention.

A taxane's anticancer activity can be determined by examining the taxane's ability to inhibit the growth of cells in vitro, for example, by incubating a cancer cell culture with the derivative, and then evaluating cell growth inhibition in the culture. Alternatively, a taxane can be tested in vivo for antitumor activity, for example, by first establishing tumors in suitable test animals, e.g., immune-deficient mice such as SCID mice, administering the taxane to the animals and then measuring tumor growth inhibition and survival rates. Cells suitable for such in vitro or in vivo testing include, without limitation: murine P388 leukemia, B16 melanoma and Lewis lung cancer cells; human breast carcinoma MCF7, human MCF-7/ADR (adriamycin-resistant), human ovarian OVCAR-3, human HT-29 colon carcinoma and A549 human lung carcinoma cells; and other cells generally accepted in the art for such testing, including those cells which are drug-resistant. Ordinarily skilled artisans given the teachings of this invention are well able to select particular taxanes for application against certain cancers, on the basis of such factors as $GI_{50}$, $ED_{50}$, survival rates and other data derived from routine in vitro or in vivo experimentation.

"Anticancer effective amounts" of a taxane are any amount of the taxane effective to ameliorate, lessen, inhibit or prevent the establishment, growth, metastasis, invasion or spread of a cancer, and can be the same amount as therapeutic doses of the corresponding free taxane. However, the attachment of an HPG-derivatized acyl chain to a taxane and the association of this taxane with a lipid carrier can enhance the taxane's therapeutic index. Thus, anticancer effective amounts of this derivatized acyl chain-taxane can also be less than those of the corresponding free taxane. Taxane anticancer effective amounts can be chosen in accordance with a number of factors, e.g., the age, size and general condition of the subject, the cancer being treated and the intended route of administration of the derivative, and determined by a variety of means, for example, dose ranging trials, well known to, and readily practiced by, ordinarily skilled artisans given the teachings of this invention. Generally, the anticancer effective amount of the taxane is at least about 0.1 mg of the taxane per kg of body weight of the animal to which the taxane-containing composition is administered. Typically, the anticancer effective amount of the taxane is from about 0.1 mg per kg of body weight of the animal to about 1000 mg per kg; preferably, the anticancer effective amount is from about 1 mg per kg to about 200 mg per kg.

Taxane-containing compositions provided herein may also comprise a lipid carrier, such as a unilamellar or multilamellar liposome. In the alternative the taxane-containing compositions of the present invention provided herein are non-liposomal and comprise the polyoxyethylated derivative of castor oil (USP/NF Polyoxyl 35 Castor Oil). Preferred anticancer taxanes have $A^1$ being the group $C_6H_5C(O)NHCH(C_6H_5)CH(OR)C(O)$—, $A^2$ being $CH_3C(O)$— and $A^3$ being H, i.e., are derivatives of paclitaxel. At least one of R or $R^1$ is preferably —$C(O)CHX^1(CH_2)_3CH_3$, —$C(O)CHX^1(CH_2)_5CH_3$, —$C(O)CHX^1(CH_2)_9CH_3$, —$C(O)CHX^1(CH_2)_{11}CH_3$ or —$C(O)CHX^1(CH_2)_{13}CH_3$, with $X^1$ preferably being F, Cl, Br or I. The $X^1$ in $CHX^1$ could have either (R) or (S) configuration or could be a mixture of (R) and (S) configurations.

Tables 3 and 4 (below) present results showing the acute toxicity of liposomal paclitaxel or the paclitaxel derivative in the mice, that is, the number of mice in each treatment group that died within the first 14 days post-injection. The results show that both of the paclitaxel derivative-containing liposomes were less toxic than were the paclitaxel-containing liposomes, with all five of the mice in the group receiving 100 mg per kg paclitaxel dying within the first 14 days. 2-Bromo-C16 paclitaxel (paclitaxel to which a sixteen-carbon acyl chain has been attached at the 2' position, the acyl chain being derivatized by the substitution of a bromine atom for an alpha carbon hydrogen atom) derivative-containing liposomes were less toxic than were the 2-bromo-C6 paclitaxel derivative-containing liposomes. Moreover, liposomes containing either paclitaxel or a 2'(2-bromo) hydrophobic paclitaxel derivative (containing either a six-carbon (C-6), C-8, C-12, C-14 or C-16 acyl chain at the 2' position) were administered, intraperitoneally in 5 doses, to scid (severe combined immunodeficiency) mice bearing a human ovarian cancer (OvCar 3), at a dose of 12.5 mg paclitaxel per kg or a dose of 50 paclitaxel derivative per kg. Results of this treatment are presented in FIG. 1, in terms of days of mouse survival post administration of either paclitaxel or a paclitaxel derivative. These results clearly show that treatment with a paclitaxel derivative extended the life span of the mice, in comparison to treatment either with paclitaxel itself or with an 'empty" liposome, i.e., a liposome containing neither paclitaxel or a paclitaxel derivative. Moreover, paclitaxel derivatives having acyl chains of increasing length were increasingly effective at extending life spans. Paclitaxel derivatives administered in non-liposomal compositions also extended the life span of tumor bearing mice in comparison to treatment with either paclitaxel itself or the non-liposomal excipient.

Furthermore, an additional bioactive agent can be administered to the animal as part of this invention's method; the additional agent is preferably, but not necessarily, a component of the taxane-containing composition, and is preferably, but not necessarily, associated with the lipid carrier when the composition contains such a carrier. Preferably, that carrier is a liposome. Liposomes can be loaded with bioactive agents by solubilizing the agent in the lipid or aqueous phase used to prepare the liposomes. Alternatively, ionizable bioactive agents can be loaded into liposomes by first forming the liposomes, establishing an electrochemical potential, e.g., by way of a pH gradient, across the outermost liposomal bilayer, and then adding the ionizable agent to the aqueous medium external to the liposome (see Bally et al. U.S. Pat. No. 5,077,056, the contents of which are incorporated herein by reference).

This invention will be better understood from the following Examples. However, those of ordinary skill in the art will readily understand that these examples are merely illustrative of the invention as defined in the claims which follow thereafter.

EXAMPLES

Example 1

Preparation of 2'-(R)-[(±)-2-Bromohexanoyl] Taxol

2'-(R)-[(±)-2-Bromo octanoyl, dodecanoyl, tetradecanoyl, and hexadecanoyl] paclitaxels were prepared (in 80–90% yield) by the procedure explained below, and identified by the $^1$H NMR and elemental analysis. To a 10 min. stirred solution of (±)-2-bromohexanoic acid (229 mg, 1.17 mmol) and 1,3-dicyclohexyl carbodiimide (241 mg, 1.17 mmol) in 30 ml of dry methylene chloride, was added taxol (500 mg, 0.586 mmol) and the base 4-dimethylaminopyridine (71.5 mg, 0.586 mmol). The reaction mixture was allowed to proceed at room temperature for 5 min. The white precipitate of dicyclohexyl urea was filtered through a Celite pad. The resultant filtrate was evaporated under vacuo and the residue obtained was purified by a preparative thin layer chromatography in CHCl$_3$:MeOH (95:5) to give the desired product (R$_f$=0.58 in CHCl$_3$:MeOH, 95:5). After passing through a Metricel filter (0.1 m) to remove the silica gel from the CHCl$_3$ solution, the product was lyophilized from cyclohexane to give 507 mg (84% yield) as the white powder.

$^1$H NMR (CDCl$_3$, 300 MHz) chemical shifts of some of the characteristic peaks at δ (in ppm): 8.14 (d, J=7.3 Hz, 2H, aromatic), 7.72( d, J=7.3 Hz, 2H, aromatic), 7.61 (m, 1H, aromatic), 7.54–7.48 (m, 3H, aromatic), 7.42–7.36 (m, 7H, aromatic), 6.87 (dd, J=2.4 Hz, 3.4 Hz, 1H, NH), 6.29 (m, 2H, H-10 and H-13), 6.0 (m, 1H, H-3') 5.68 (d, J=6.9 Hz, 1H, H-2b), 5.50 (dd, J=1.4 Hz, 1.0 Hz, 1H, H-2'), 4.97 (d, J=7.8 Hz, 1H, H-5), 4.45 (m, 1H, H-7), 4.32 (d, J=7.3 Hz, 1H, H-20a), 4.28 (m, 1H, CH(Br)), 4.20 (d, J=8.3 Hz, 1H, H-20b), 4.0 (br, OH), 3.81 (d, J=6.9 Hz, 1H, H-3), 0.86 (app. †. 3H, w-CH$_3$). FABMS: (MH$^+$) calcd for C$_{53}$H$_{60}$NO$_{15}$Br 1029.32. Found 1030.

Scheme I: Route to the synthesis of 2'-(R)-[(±)-2-Bromoacyl] paclitaxels ("DCC"=1,3-dicyclohexylcarbodiimide' "DMAP"=4-dimethylaminopyridine)

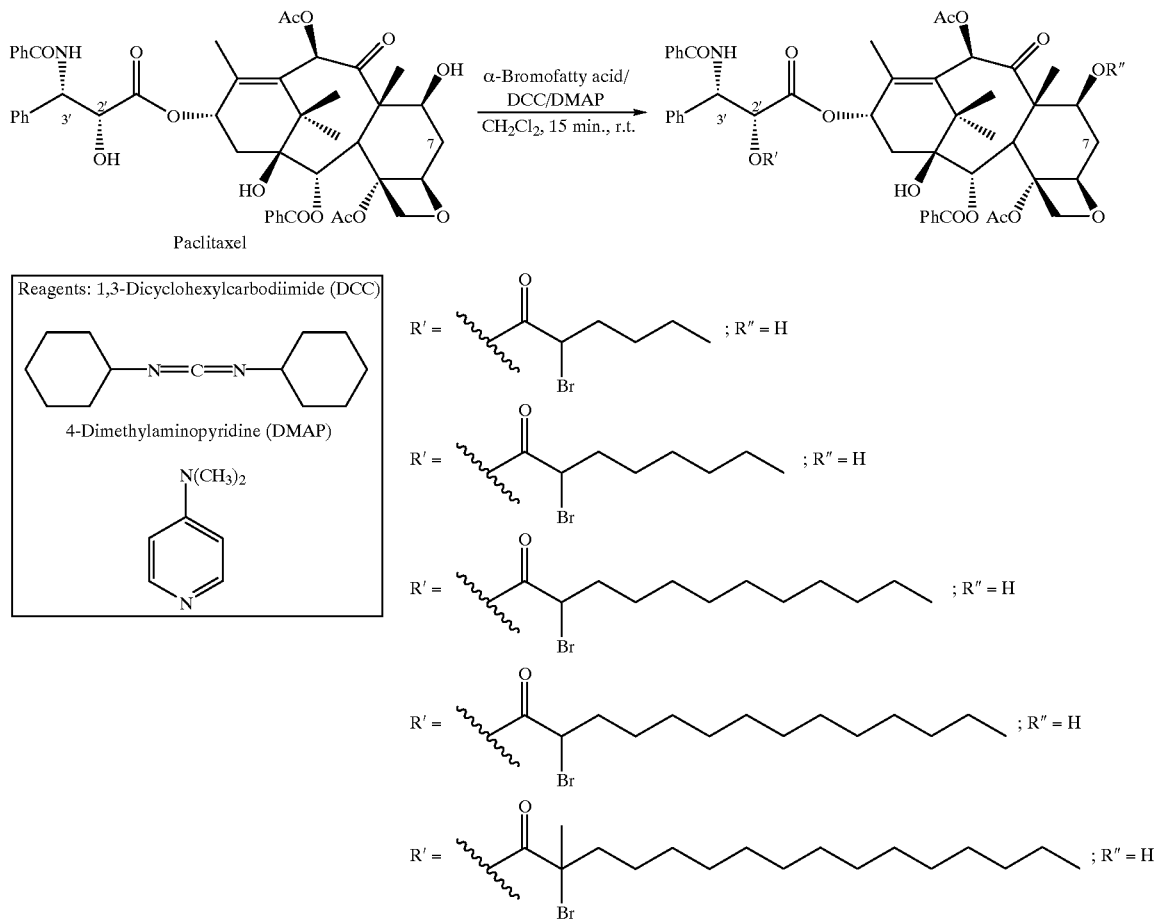

Example 2

Preparation of 2'(R)-[2-(R)-Bromohexadecanoyl and 2'-(R)-[2-(S)-Bromohexadecanoyl Taxol

One can obtain the α-substituted acyl chain having a high enantiomeric excess of either isomer either by preparing the single enantiomer synthetically or by isolating the single enantiomer from a mixture of optical isomers. The individual enantiomers of the α-substituted fatty acids may then be used to synthesize taxanes with α-substituted carbonyl compounds esterified to the 2' or 7 hydroxy position. The single enantiomer product can be coupled to paclitaxel according to the method described in Example 1 above.

For instance, in order to allow enzymatic preparation of a single stereoisomer, the (±)-2-bromohexadecanoic acid was first converted to a methyl ester (fatty acid methyl esters (FAME)) to form an enzyme substrate. This was followed by reaction with a stereospecific enzyme that cleaved the methyl group from one enantiomer.

For example,

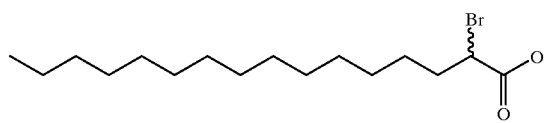

(±)-2-bromo hexadecanoyl fatty acid was converted to the methyl esters,

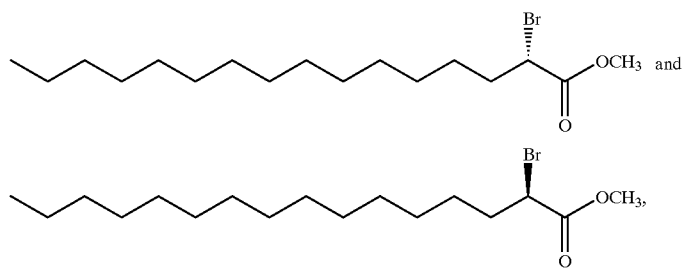

forming methyl esters of both enantiomers.

Reaction of the racemic mixture with a sterospecific enzyme cleaved the methyl group from only one enantiomer, leaving the second enantiomer methylated.

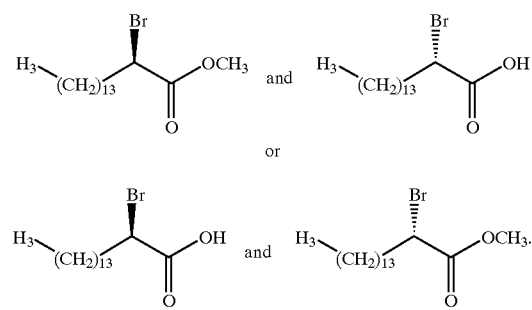

The methylated compound can be separated from the carboxylic acid by methods known to those skilled in the art. One method comprises separation utilizing chromatography. After the methylated and hydroxy fatty acids are separated, a fatty acid comprising a single enantiomer can be coupled to the taxane as described in Example 1. The opposite enantiomer can be demethylated by using chemical rather than enzymatic means and can be used as described in Example 1 to prepare enantiomerically pure or enriched acyl chain derivatives of the taxanes.

For example, the fatty acid used in Example 1, (±)-2-Bromohexadecanoic acid was converted to the methyl ester by refluxing 17 g of the fatty acid dissolved in 100 mL CH$_3$OH, and 2 mL of H$_2$SO$_4$ for 2 hrs. Next, an enzymatic reaction was carried out by incubating 300 mg of FAME in 24 mL of THF: 0.1 mM, pH 7.0, phosphate butter (2:1) with 120 mg (30,000 U/g) of Lipase "Amano" PS (*Pseudomonas cepacia*) for 24 hrs at room temperature. FIG. 2 demonstrates the time dependence of the Lipase reaction. Samples of the FAME with (FIG. 2-A left lane) and without lipase (FIG. 2-A right lane) were withdrawn from the reaction vessels at various times during the course of the reaction and were spotted on silica TLC plates. The spot at the top of the plate corresponded with the R$_f$ of the FAME and the lower spot corresponded to the R$_f$ of the fatty acid. The reaction with enzyme proceeded much faster than the non-enzymatic reaction. The enzymatic conversion was optimized by adding to a solution of 1.0 g of methyl 2-bromohexadecanoate in 29.3 mL THF (freshly distilled from lithium aluminum hydride), 14.7 mL of phosphate buffer (0.1 M, pH 7.0), 300 mg of lipase "Amano" P S (*Pseudomonas cepacia*, 3,000, 000 U/g). The reaction was stirred in dark for 2 hours at RT and followed by thin layer chromatography (TLC) (hexane/ethyl acetate/acetic acid, 4 mL/1 mL/1 drop).

Figure 2B:
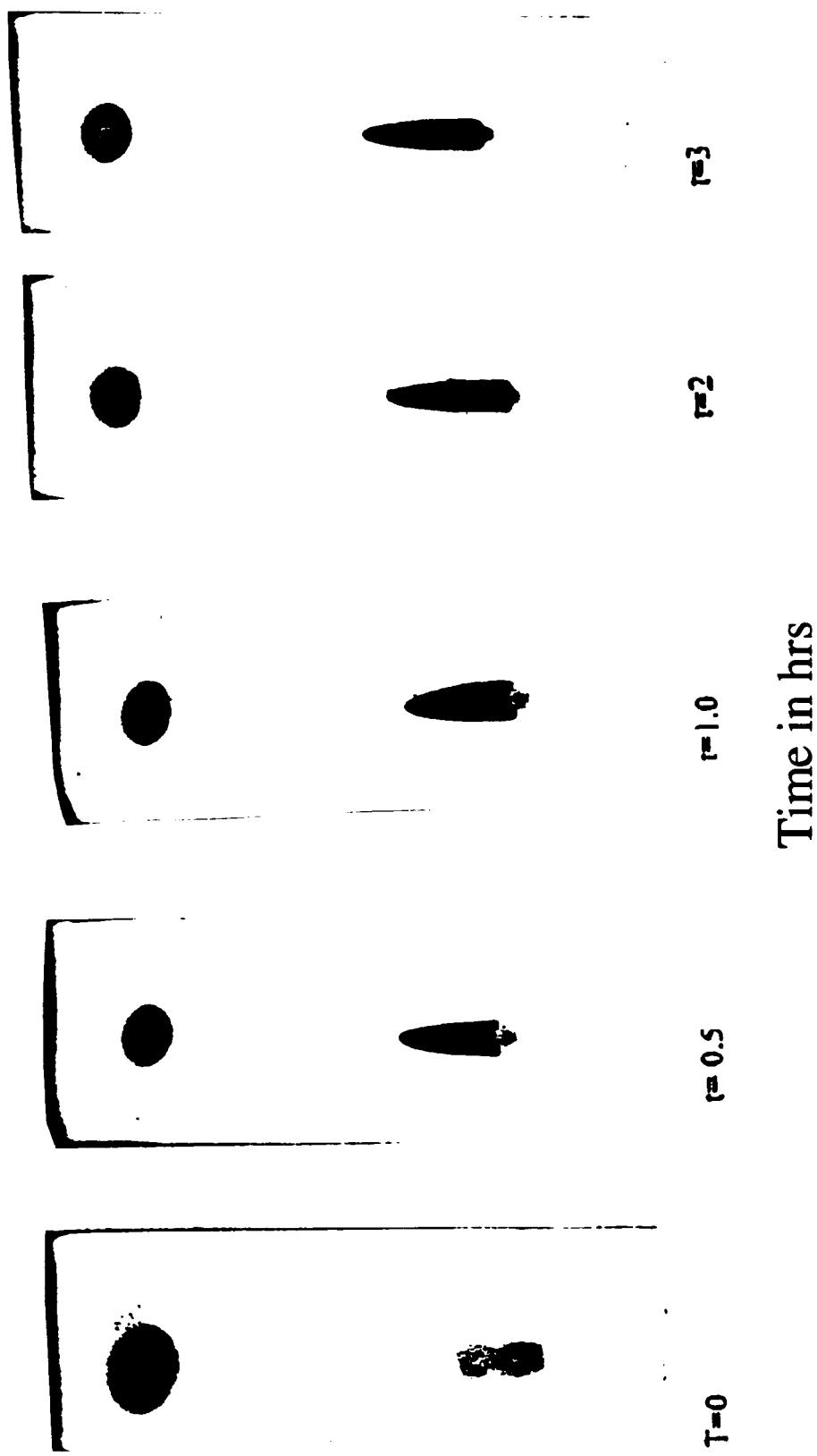

FIG. 2B shows that under these conditions the FAME was converted to the carboxylate in less than 30 min, followed by a peroid of about 3 hours without noticeable change. Although TLC under these conditions was not quantitative, the equal density of the fatty acid and FAME at equilibrium suggested a high degree of stereoselectivity.

Figure 3A:
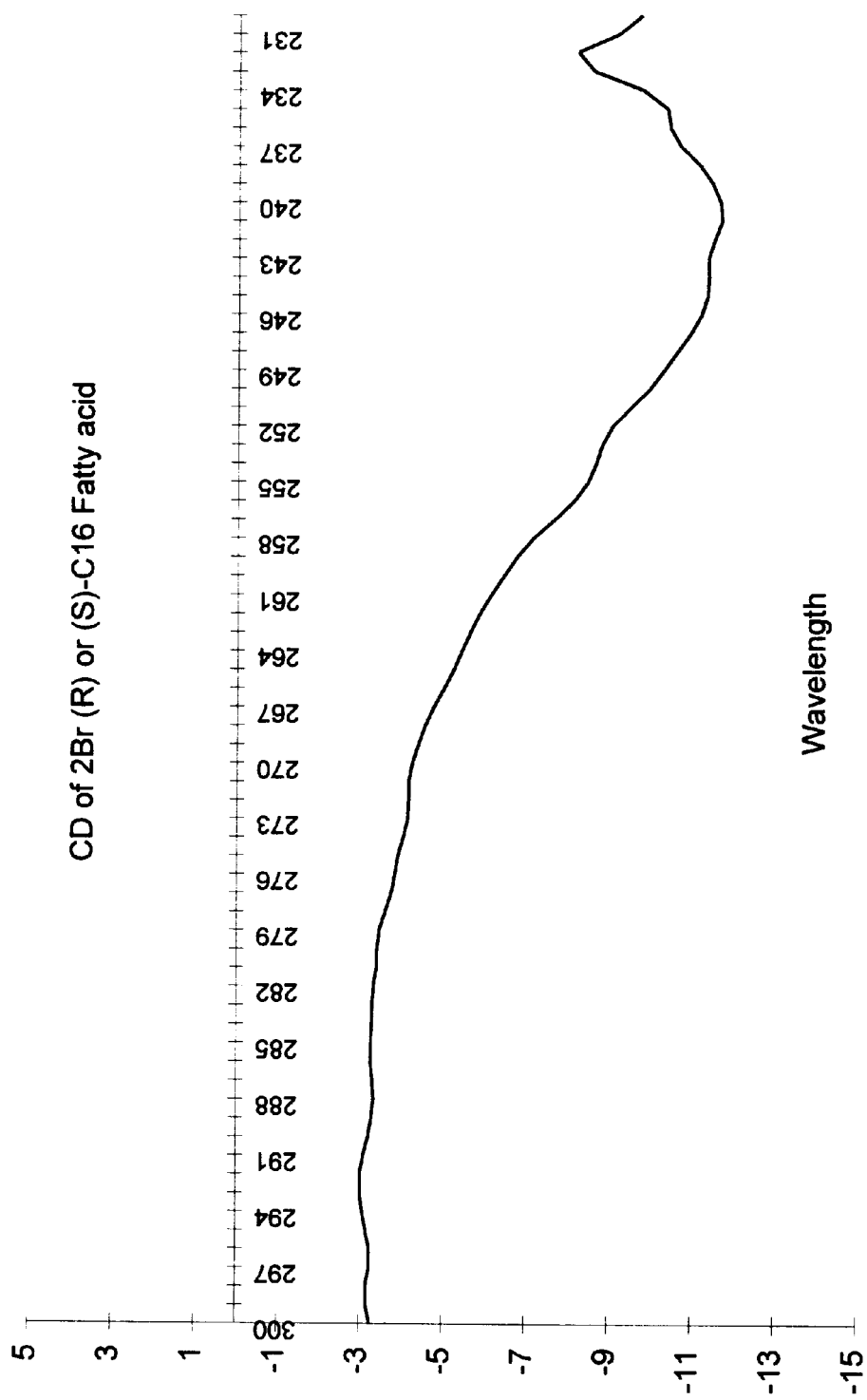
FIG. 3. CD spectrum of (±)-2-bromohexadecanoyl methyl ester FAME after and before enzymatic cleavage by *Pseudomonas cepacacia* lipase (3A and 3B, respectively).
Figure 3B:
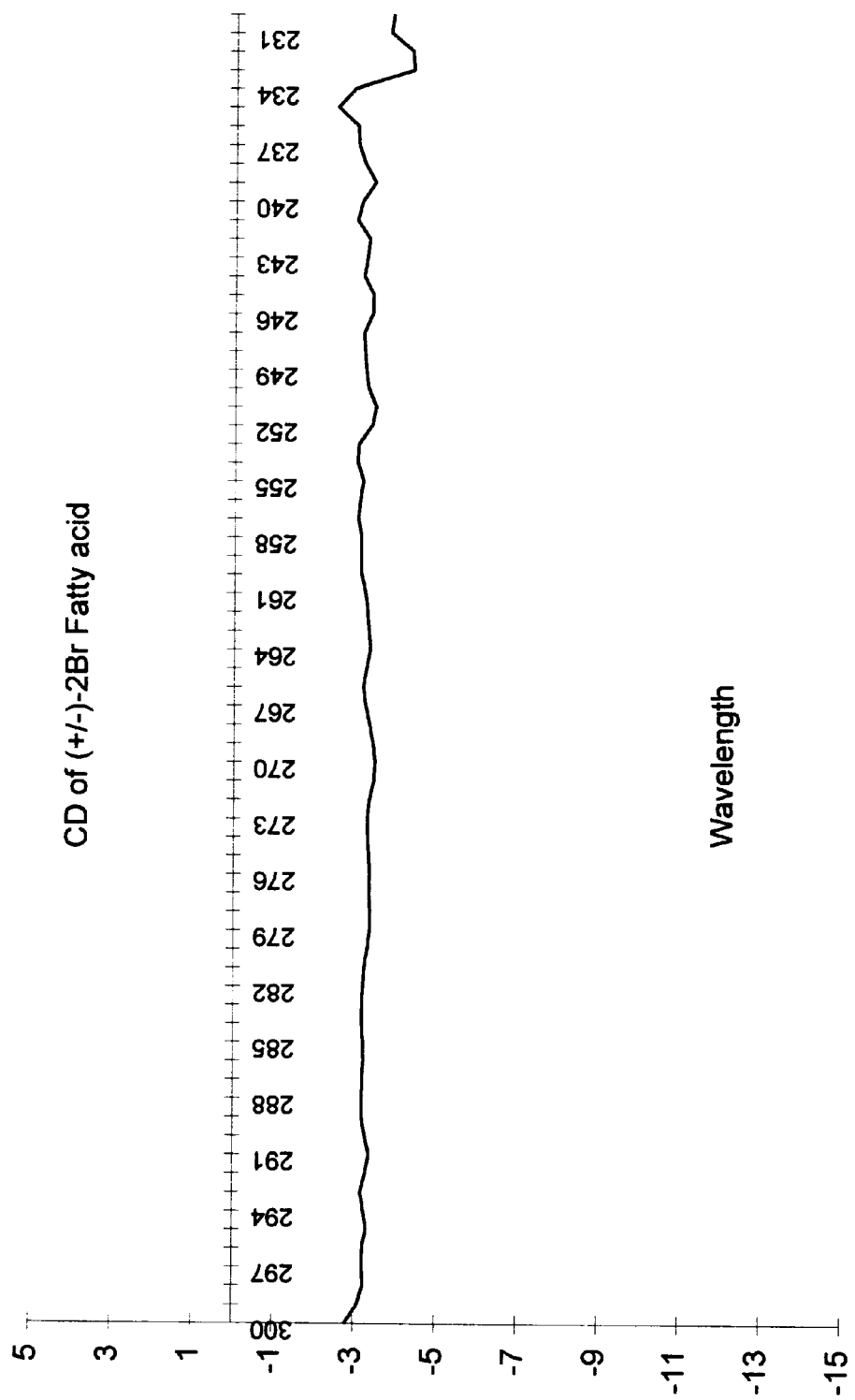

The CD spectrum of the fatty acid prior to and following enzymatic cleavage are plotted in FIG. 3. The negative values in FIG. 3A are the consequence of the selective adsorption of polarized light due to the higher concentration of one enantiomer. The racemic mixture (pre enzymatic cleavage, FIG. 3B) in the lower figure did not rotate polarized light. FIG. 4 plots the CD spectrum of FAME remaining after enzymatic cleavage as compared with FAMEs prior to enzymatic cleavage. Again, incubation of FAMEs with enzymes resulted in the formation of FAMEs that adsorb polarized light indicating an enantomeric excess.

In order to prepare single enantiomers that were of opposite rotation from the enantiomers prepared enzymatically above, fatty acids were separated from unhydrolyzed methyl esters. For example approximately 1 gram of the enzyme reaction mixture was loaded on to a 4×30 cm silica gel 60 column and eluted with a gradient ranging from hexane-ethyl (15:1) acetate to pure hexane. The unchanged methyl esters were then chemically hydrolyzed to fatty acids. For example, 50 mg of ester dissolved in 3 mL THF were mixed with 1 mL of 0.1 N NaOH and stirred at room temperature for 2 hrs. This chemical cleavage results in the formation of the isomer not cleaved in the enzymatic reaction. The specific rotation of the material prior to separation was 0.0°/g cm. The specific rotation of the fatty acid formed through enzymatic cleavage was −23.1°/g cm and the specific rotation of the fatty acid derived from the methyl ester following enzymatic cleavage was 18.4°/g cm.

Each of the fatty acid enantiomers were then reacted in place of the racemic fatty acid mixture in Example 1 to produce enantiomerically enriched taxanes, i.e., 2'-(R)-[2-(R)-Bromohexanoyl] taxol and 2'-(R)-[2-(S)-Bromohexanoyl] taxol.

Example 3

In Vitro Studies

Table 1 (see below) shows the GI$_{50}$ (µM) values (± standard deviation), that is, the concentration required for 50% growth inhibition, of various hydrolyzable taxane derivatives (HTDs) and human MCF-7 breast carcinoma cells following a 72-hour incubation of the cells with the HTD.

TABLE 1

HTD CYTOTOXICITY

| Paclitaxel Derivative | $GI_{50}$ |
|---|---|
| 2'-Hexanoyl- | 0.500 ± 0.151 |
| 2'-2-Bromohexanoyl- | 0.003 ± 0.0002 |
| 2'-6-Bromohexanoyl- | >10.000 |
| 7-Hexanoyl- | 0.027 ± 0.019 |
| 7-2-Bromohexanoyl- | 0.0046 ± 0.0001 |
| 7-6-Bromohexanoyl- | 0.018 ± 0.002 |
| 2'-Acetyl-7-Hexanoyl- | 4.46 ± 0.06 |
| 2',7-di-2-Bromohexanoyl- | 1.43 ± 0.72 |
| 2',7-diHexanoyl- | >10.00 |
| 2'-Troc-7-2-Bromohexanoyl- | 2.67 ± 0.08 |
| 2'-Troc-7-6-Bromohexanoyl- | 0.47 ± 0.03 |

"2'" indicates attachment of an acyl chain to paclitaxel at the 2' position; "7'": attachment at the 7' position; "bromo": derivatization of an attached acyl chain with a bromine atom.

Table 2 (see below) shows the $GI_{50}$ ($\mu$M) values, averaged from two separate experiments (the sulforhodamine B SRB standard cytotoxicity assay as described in Example 5, below), for paclitaxel and various 2'-2-bromo paclitaxel derivatives and A-549 human lung carcinoma, MCF-7 human breast carcinoma, MCF-7/ADR (adriamycin-resistant) and HT-29 human colon carcinoma cells following a 72-hour incubation of the cells and HTDs ("C-6, 8, 12, 14 and 16"): 6, 8, 12, 14 and 16-carbon acyl chains, respectively, attached to paclitaxel).

TABLE 2

In Vitro Sensitivity

| HTD | A-549 | MCF-7 | MCF-7/ADR | HT-29 |
|---|---|---|---|---|
| Paclitaxel | 0.0023 ± 0.0002 | <0.0015 | 4.1675 ± 0.7177 | <0.0014 |
| 2'-2-Bromo-C6-Paclitaxel | 0.0039 ± 0.0008 | 0.0023 ± 0.0013 | >10.0000 | 0.0024 ± 0.0009 |
| 2'-2-Bromo-C8-Paclitaxel | 0.0044 ± 0.0001 | 0.0029 ± 0.0010 | >10.0000 | 0.0031 ± 0.0003 |
| 2'-2-Bromo-C12-Paclitaxel | 0.0044 ± 0.0001 | 0.0028 ± 0.0007 | >10.0000 | 0.0032 ± 0.0002 |
| 2'-2-Bromo-C14-Paclitaxel | 0.0317 ± 0.0047 | 0.0160 ± 0.0091 | >10.0000 | 0.0206 ± 0.0057 |
| 2'-2-Bromo-C16-Paclitaxel | 0.1273 ± 0.0356 | 0.0710 ± 0.0373 | >10.0000 | 0.0595 ± 0.0187 |

Example 4

In vivo Studies

CDF1 female mice, 5 or 10 mice per group, were intraperitoneally administered either paclitaxel-, 2'-C6-paclitaxel derivative-, or 2'-C16-paclitaxel derivative-containing liposomes, in a single dose, or 5 doses, of either 12.5, 25, 50, 100, 200, 300, 400 or 500 mg of paclitaxel or paclitaxel derivative per kg of mouse body weight. Tables 3 and 4 (below) present results showing the acute toxicity of paclitaxel or the paclitaxel derivative in the mice, that is, the number of mice in each treatment group that died within the first 14 days post-injection. The results show that both of the paclitaxel derivative-containing liposomes were less toxic than were the paclitaxel-containing liposomes, with all five of the mice in the group receiving 100 mg per kg paclitaxel dying within the first 14 days. 2-Bromo-C16 paclitaxel derivative-containing liposomes were less toxic than were the 2-bromo-C6 paclitaxel derivative-containing liposomes.

TABLE 3

SINGLE DOSE ADMINISTRATION

| | | Paclitaxel Derivative | |
|---|---|---|---|
| Dose (mg/kg) | Paclitaxel | 2-BrC6HT | 2-Br-C16HT |
| 500 | — | 5/5 | 0/5 |
| 400 | — | 5/5 | 1/5 |
| 300 | — | 4/5 | 1/5 |
| 200 | — | 0/2 | — |
| 100 | 5/5 | — | — |
| 50 | 0/10 | — | — |
| 25 | 0/10 | — | — |
| 12.5 | 0/10 | — | — |

TABLE 4

FIVE DOSE ADMINISTRATION

| Dose (mg/kg) | Paclitaxel | 2-BrC6 Paclitaxel Derivative |
|---|---|---|
| 50 | 10/10 | 0/5 |
| 25 | 10/10 | — |
| 12.5 | 0/10 | — |

Liposomes containing either paclitaxel or a 2'-(2-bromo) hydrophobic paclitaxel derivative (containing either a six-carbon (C-6), C-8, C-12, C-14 or C-16 acyl chain at the 2' position) were administered, intraperitoneally in 5 doses, to scid (severe combined immunodeficiency) mice bearing a human ovarian cancer (OvCar 3), at a dose of 12.5 m paclitaxel per kg or a dose of 50 paclitaxel derivative per kg. Results of this treatment are presented in FIG. 1, in terms of days of mouse survival post administration of either paclitaxel or a paclitaxel derivative. These results clearly show that treatment with a paclitaxel derivative extended the life span of the mice, in comparison to treatment either with paclitaxel itself or with an 'empty' liposome, i.e., a liposome containing neither paclitaxel or a paclitaxel derivative. Moreover, paclitaxel derivatives having acyl chains of increasing length were increasingly effective at extending life spans.

Example 5

In Vitro Growth Inhibition of Bromo Hexadecanoyl Paclitaxel

The growth inhibitory effects of BrC16HT or Taxol® in human (A549, OVCAR-3) cancer cells was measured by the sulforhodamine B (SRB) assay (Monks, et al. J. Natl. Cancer Inst. 38:757–766, 1991; Skehan, et al. J. Natl. Cancer Inst., 82:1107–1112, 1990). This assay was used to determine relative in vitro drug sensitivity using the $GI_{50}$ parameter (the calculated concentration of test material which inhibits 50% cell growth). Briefly, 96-well microtiter plates were inoculated (100 $\mu$L/well) with 5×10³ (A549) or 7.5×10³ (OVCAR-3) cells/well, in RPMI-1640 supplemented with 10% FBS (growth media). The plates were incubated for 24 hr at 37° C., 100% humidity and 5% $CO_2$. At 24 hours, growth media (100 $\mu$L) was added to designated "time zero" plates. Similarly, serial dilutions of drug or vehicle (in media) were added (100 $\mu$L aliquots) to the test and vehicle control wells at twice the predetermined highest concentration. There were triplicate wells on each plate and duplicate plates (total 6 wells) for each drug concentration. The test plates were incubated as above for 72 hr. Cells (including time zero plates) were then fixed with 50 μL of 50% trichloroacetic acid (TCA) (w:v) for adherent cells or 80% TCA for suspended cells, and plates refrigerated at 4° C. for 1 hr. The supernatant was discarded (suspended cell plates were first centrifuged) and the wells rinsed six times with tap water and air-dried. One hundred microliters of 0.4% SRB in 1% acetic acid were added to each well and the plates were incubated under ambient (RT) conditions for 10 min. Unbound stain was removed by rinsing the wells three times with 1% acetic acid. The plates were then air-dried for 24 hr. The bound stain was solubilized with 100 μL of 10 mM Tris buffer and the optical density was read spectrophotometrically at 490 nm (Microplate Reader Model 3550-UV, Bio-Rad, Hercules, Calif.). Percent growth was calculated as follows: $(T-T_0)/(C-T_0) \times 100$; where (T)=mean optical density of treated wells at a given drug concentration, $(T_0)$= mean optical density of time zero wells, and (C)=mean optical density of control wells. If $T<T_0$, which indicates that cell death has occurred, then percent cell death was calculated as $(T-T_0)/(T_0) \times 100$. Dose response curves were generated and $GI_{50}$ values calculated using data obtained from the six wells is shown on Table 5.

The results demonstrate that the BrC16HT $GI_{50}$ values were approximately ten times higher than Taxol® in both cell lines. thus, providing further evidence that BrC16HT is a prodrug which is converted to the biologically active form in vivo.

TABLE 5

In vitro cytotoxicity of BrC16HT and Taxol ®

| Tumor Cell Line | *$GI_{50}$ (nM) ± S.D. | |
|---|---|---|
| | BrC16HT | Taxol ® |
| A549 | 29 ± 5.9 | 3.3 ± 0.8 |
| OVCAR-3 | 20 ± 3.3 | 1.9 ± 0.03 |

*$GI_{50}$ = concentration of drug required to inhibit cell growth by 50%.

Example 6

Hydrolysis in Murine Plasma

In order to demonstrate that BrC16HT is a prodrug which is converted in the animal to the active anticancer agent, BrC16HT and Taxol were incubated with plasma in vitro and the concentration of paclitaxel was assessed after various times of incubation.

Briefly, blood was collected from CDF1 mice (via heart puncture) into 1 cc syringes containing 0.05 mL of a 0.129M Sodium Citrate solution (Baxter, N.J.). Samples were centrifuged at 2000× g for 10 min and plasma was removed and pooled. BrC16HT or Taxol® were diluted in PBS to a final concentration of 1 mg/mL. Plasma (225 μl) was incubated with BrC16HT or Taxol® at final concentrations of 25, 50 or 100 μg/mL (3 samples per group, final volume 250 μL). Samples were extracted immediately (0 hr) or incubated at 37° C. for 24 hr. Extraction from plasma was done by adding 237.5 μL of acetonitrile and 12.5 μL of internal standard solution (2C12-HT, 50 μg/ml in acetonitrile, which was found to elute between BrC16HT and paclitaxel peaks) to each sample and vortexing vigorously for 30 sec. Samples were then centrifuged for 3 min at 10,000× g, and 300 μL of each supernatant analyzed by HPLC. The chromatographic system consisted of a Waters 600 pump, Waters 712 WISP, and Spectroflow 757 UV detector. The column used was an Inertsil-ODS 2, 150×4.6 mm (5 micron particle size) from Keystone Scientific (Bellefonte, Pa.). A 20 μL injection at ambient temperature was read at 227 nm. Extraction efficiency was approximately 95%, with a linear standard curve ($R^2$=0.998), from 6.25–100 μg/mL. The mobil phase consisted of water/acetonitrile (75%/25%) and acetonitrile (100%), and the gradient was: 70/30 (5 min), 30/70 (5 min), 0/100 (5 min), hold (5 min), 40/60 (5 min), and 70/30 (5 min) to equilibrate. The constant flow rate was 1 mL/min.

Figure 5:
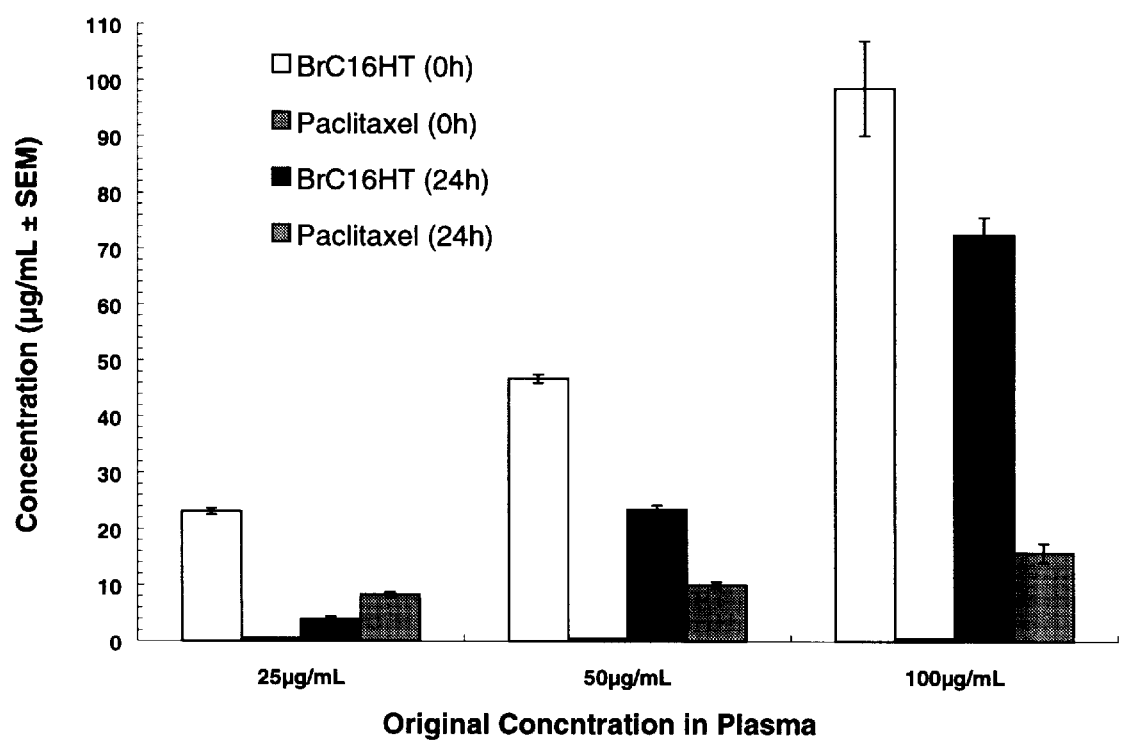
FIG. 5 Hydrolysis of BrC16HT to paclitaxel in murine plasma. Plasma samples (3/group) were incubated with 25, 50 or 100 ug/mL of BrC16HT. BrC16HT and paclitaxel concentrations were determined at 0 hr and after 24 hr at 37° C. via HPLC.

FIG. 5 shows the HPLC results of 24 hr incubation of BrC16HT in mouse plasma at 37° C. Hydrolysis of BrC16HT to paclitaxel is shown by the appearance of paclitaxel after 24 hr. At time zero there was no detectable paclitaxel peak, with recovery of BrC16HT approximately 95%. Although various concentrations of BrC16HT were tested, at 24 hr the plasma contained similar concentrations of paclitaxel (8.3 to 15.7 μg/mL), which suggests that the plasma:drug ratio may be a limiting factor in BrC16HT conversion to paclitaxel in in vitro experiments. Typical HPLC elution times for Taxol,® the internal standard 2C12-HT, and BrC16HT were 7.4, 18.4 and 22.2 min respectively (data not shown).

Example 7

In Vivo Toxicity Studies

In order to demonstrate the toxicity of BrC16HT as compared to Taxol® in vivo in normal animals, groups of non-tumor bearing CDF1 mice were injected with one injection per day for five consecutive days i.p. (2–25/group at 25 mL/kg dose volume) or i.v. (7–10/group, 15 mL/kg) with BrC16HT or Taxol.® For comparison with Taxol®, BrC16Ht was solubilized at a concentration of 6 mg/ml in a 50/50 (v/v) mixture of ethanol and Cremophor® EL. The molecular weight of BrC16HT is approximately 27% greater than paclitaxel. For animal dosing, mice were injected based upon compound weight (mg/kg), therefore at equivalent doses of BrC16HT or Taxol,® mice received 27% less (by weight) paclitaxel when dosed with BrC16HT. A separate group (n=5) was injected with concentrations of Cremophor® EL and ethanol (in PBS) equivalent to the highest concentration of the test treatment. Mortality was recorded daily and body weights taken at least twice weekly for an observation period of 30 days.

Tables 6 and 7 show the multiple dose i.p. and i.v. toxicity of BrC16HT and Taxol® in non-tumor bearing CDF1 mice. The results shown on Table 6 demonstrate that the maximum tolerated i.p. dose (MTD, or highest dose with no deaths) of BrC16HT given once daily for five consecutive days was between 37.5 and 50 mg/kg. Under the same conditions the MTD of Taxol® was between 12.5 and 25 mg/kg. The MTD for five i.v. daily doses of both compounds was similar (Table 7). For both routes, less than 5% body weight loss from initial was seen for both test compounds at their respective MTD (data not shown).

TABLE 6

Toxicity of BrC16HT vs. Taxol ® in CDF1 mice
(i.p. × 5)

| Dose | Number of Mice surviving/Total | |
|---|---|---|
| mg/kg | BrC16HT | Taxol ® |
| 12.5 | 10/10 | 20/20 |
| 25 | 19/19 | 10/20 |
| 37.5 | 10/10 | 0/10 |
| 50 | 14/20 | 0/25 |
| 75 | 0/5 | — |
| 100 | 0/2 | — |

Toxicity of BrC16HT in female CDF1 mice. Mice (n=2–25/group) were treated on days 1 through 5 intraperitoneally. Drugs were all diluted in PBS (control) and delivered at a dose volume of 25 mL/kg. Mortality was checked daily and body weights and observations taken twice weekly for 30 days.

TABLE 7

Toxicity of BrC16HT vs. Taxol ® in CDF1 mice
(i.v. × 5)

| Dose | Number of Mice surviving/Total | |
|---|---|---|
| mg/kg | BrC16HT | Taxol ® |
| 12.5 | 10/10 | 10/10 |
| 25 | 9/10 | 8/10 |
| 37.5 | 0/10 | 0/7 |
| 50 | 0/10 | 0/8 |

Toxicity of BrC16HT in female CDF1 mice. Mice (n=7–10/group) were treated on days 1 through 5 intravenously. Drugs were all diluted in PBS (control) and delivered at a dose volume of 15 mL/kg. Mortality was checked daily and body weights and observations taken twice weekly for 30 days.

Example 8

Pharmacokinetic

CDF1 mice (4/group) were injected i.v. with BrC16HT or Taxol® (25 mg/kg). Control mice received an equivalent concentration of Cremophor® EL and ethanol (in PBS) only. At 1, 4, 8, 24 or 48 hr after injection mice were sacrificed and blood was collected via heart puncture into 1 cc syringes containing 0.05 mL of a 0.129M Sodium citrate solution (Baxter, N.J.). Samples were centrifuged at 10,000× g for 3 min and plasma removed. Extraction of test materials from plasma was done by adding an equal volume of acetonitrile containing 2C12-HT, 50 $\mu$g/ml, as an internal standard, and vortexing vigorously for 30 sec. Samples were then centrifuged for 3 min at 10,000× g and supernatant and drug levels determined via HPLC as described previously.

Table 8 shows that paclitaxel (from Taxol®) was cleared quickly from circulation after administration, with none detectable 8 hr after administration. In contrast, BrC16HT levels were detectable for at least 24 hr after administration. Paclitaxel generated from BrC16HT was detectable for 24 hr and was at substantial levels for at least 8 hr. The results suggest that BrC16HT may be slowly hydrolyzed to paclitaxel, resulting in sustained and increased availability of the active component, paclitaxel.

TABLE 8

Plasma levels (ug/ml ± SEM) of BrC16HT and Paclitaxel after
i.v. administration of
25 mg/kg BrC16HT or Taxol ® in CDF1 Female Mice

| Time | Taxol ® | BrC16HT (Crem/EtOH) | |
|---|---|---|---|
| Hours | paclitaxel | paclitaxel | BrC16HT |
| 1 | 14.4 ± 4.6 | 27.5 ± 5.7 | 341 ± 40.0 |
| 4 | <5.0* | 16.8 ± 7.0 | 239 ± 15.4 |
| 8 | ND** | 15.4 ± 5.8 | 204 ± 23.0 |
| 24 | ND** | <5.0* | 72.7 ± 7.6 |
| 48 | ND** | ND** | ND** |

*Small peak detected on chromatograph, concentration not calculated.
**ND = not detected, no peak observed Example 9

Anti-tumor Studies in Mice

Four tumor models were used: intraperitoneal (i.p.) OVCAR-3 human ovarian cancer or A549 human NSCLC, or subcutaneous (s.c.) OVCAR-3 or A549. The ascitic model was chosen to model tumors which spread via the peritoneal cavity, such as ovarian cancer. The s.c. tumor were used to model human solid tumor and allow measurement of tumor volume over time.

A. OVCAR-3 Human Ovarian Cancer

1. I.p. Tumor, I.p. Treatment

C.B-17 SCID female mice were injected i.p. with 5×10$^6$ OVCAR-3 human ovarian cancer cells (day 0). On days 1, 3, 5, 7 & 9 (5/group) or 20, 22, 24, 26 & 28 (10/group) mice were treated i.p. with BrC16HT, Taxol® or vehicle. Mice were observed daily for mortality and percent increased life span (% ILS) was calculated as: [(mean survival time in days (MST) of treatment group/MST of control)×100]−100. Note that long-term survivors (mice that survived through day 300 after cell inoculation) were not included in mean, median, or % ILS calculations.

Table 9 shows that BrC16HT or Taxol® significantly prolonged (p<0.05 vs. control) the survival of tumor-bearing mice both in early (days 1, 3, 5, 7 & 9; Table 9a) and delayed (days 20, 22, 24, 26 & 28; Table 9b) i.p. treatment schedules. In both cases, at equivalent doses BrC16HT was more effective than Taxol® in extending survival time. In the delayed schedule, Taxol® doses of 12.5 or 25 mg/kg×5 i.p. were equally effective; median survival times were 178 and 185 days, respectively. BrC16HT, (which was able to be administered at higher doses) vs. the highest testable Taxol® treatment, showed an increased survival time, with median survival times for BrC16HT at 12.5, 25 and 50 mg/kg of 237, 221 and 245 days, respectively (Table 9b). These values do not include long-term surviving (LTS, i.e. mice that survived to the study termination at 300 days) mice. BrC16HT showed a clear dose-response effect with regard to LTS, yet no long-term survivors were observed in Taxol® groups (Table 9b). BrC16HT also significantly increased survival at both 25 and 50 mg/kg when compared to Taxol® 25 mg/kg (p<0.02).

TABLE 9

Administration of BrC16HT i.p. Against i.p. OVCAR-3 Tumors

| Treatment Group | Dose (mg/kg) | MST Days ± SEM(n) | % ILS | Median | LTS/n |
|---|---|---|---|---|---|
| A: OVCAR-3 tumor i.p. Treated days 1, 3, 5,7 and 9 i.p. | | | | | |
| Control | Crem/EtOH | 73 ± 9(5) | — | 75 | 0/5 |
| Taxol | 12.5 | 145 ± 8(5) | 99 | 145 | 0/5 |
| BrC16HT | 12.5 | 257 ± 15(3) | 252 | 245 | 2/5 |
| B: OVCAR-3 tumor i.p. Treated days 20, 22, 24, 26 and 28 i.p. | | | | | |
| Control | Crem/EtOH | 102 ± 7(10) | — | 93 | 0/10 |
| Taxol | 12.5 | 187 ± 14(10) | 84 | 178 | 0/10 |
| Taxol | 25 | 188 ± 15(10) | 84 | 185 | 0/10 |
| BrC16HT | 12.5 | 200 ± 30(8) | 96 | 237 | 2/10 |
| BrC16HT | 25 | 220 ± 13(6) | 115 | 221 | 4/10 |
| BrC16HT | 50 | 183 ± 67(3) | 80 | 245 | 7/10 |

2. I.p. Tumor, i.v. Treatment

To compare the effect of i.v. rather i.p. administration of BrC16HT and Taxol, SCID mice were injected ip. with $5 \times 10^6$ OVCAR-3 cells (day 0). On days 1, 3, 5, 7, 9, 41, 43, 45, 47 & 49 mice were treated i.v. with BrC16HT or Taxol® (12.5 or 25 mg/kg) or vehicle (5/group). To determine the efficacy of delayed treatment, mice injected on day 0 with OVCAR-3 cells were treated i.v. on days 20, 22, 24, 26 & 28 with BrC16HT (12.5 or 25 mg/kg), Taxol® (12.5 mg/kg) or vehicle (10/group). Mice were observed daily for mortality and %ILS was calculated as described above.

Figure 6A:
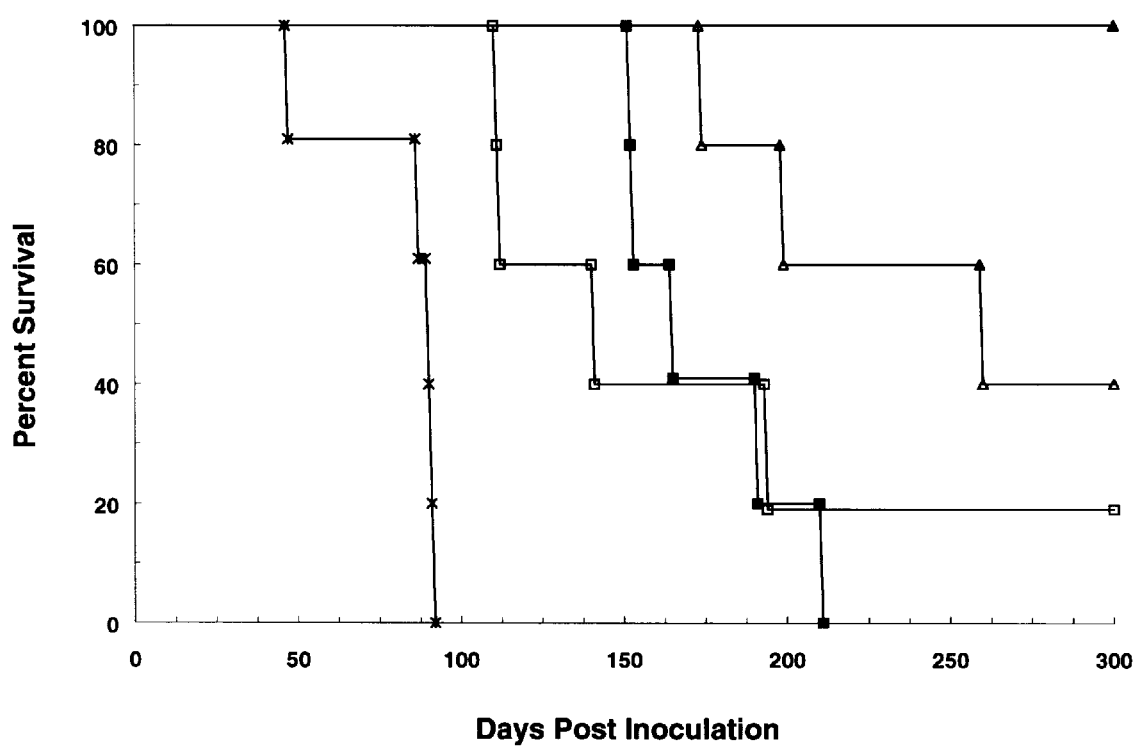
FIG. 6 Effect of BrC16HT administered i.v. against i.p. OVCAR-3 human ovarian cancer. C.B-17 SCID female mice were inoculated with 5×10⁶ OVCAR-3 cells ip. and were treated with (Δ) BrC16HT 12.5 mg/kg, (▲) BrC16HT 25 mg/kg, (□) Taxol® 12.5 mg/kg, (■) Taxol® 25 mg/kg or (*) control iv. on days a) 1, 3, 5, 7, 9, 41, 43, 45, 47 & 49 (5/group) or b) 20, 22, 24, 26 & 28 (10/group).
Figure 6B:
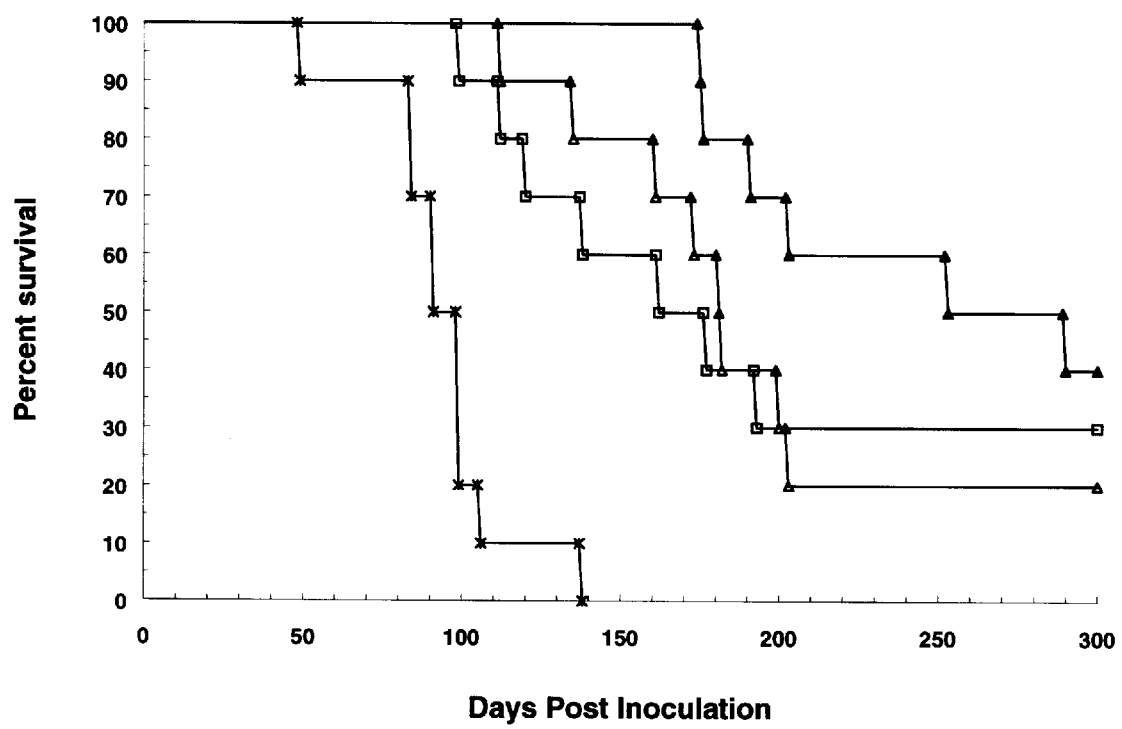

FIG. 6a shows that BrC16HT or Taxol® (12.5 or 25 mg/kg) administered i.v. on days 1, 3, 5, 7, 9, 42, 44, 46, 48 & 50 significantly ($p<0.05$ vs. control) increased the survival time of OVCAR-3 (i.p.) tumor-bearing mice. BrC16HT at both dosages (12.5 or 25 mg/kg), open and solid triangles, respectively, was more effective than Taxol.® FIG. 6b shows that BrC16HT (12.5 or 25 mg/kg), open squares or Taxol® (12.5 mg/kg) administered i.v. on days 20, 22, 24, 26 & 28 significantly ($p<0.05$ vs. control) increased the survival time of OVCAR-3 (i.p.) tumor-bearing mice. BrC16HT at 12.5 mg/kg was found to be at least as effective as Taxol® at 12.5 mg/kg, with median survival times of 182 and 170 days, respectively. BrC16HT also showed dose-related % ILS: at 25 mg/kg, survival time was significantly prolonged compared to controls ($p<0.0001$).

3. S.c. Tumor. i.v. Treatment

To determine the effect of the drugs on a solid tumor model, SCID mice (5/group) were injected s.c. with $2 \times 10^6$ OVCAR-3 cells (day 0). Treatments were administered i.v. on days 1, 3, 5, 7 & 9 with BrC16HT (12.5–25 mg/kg), Taxol® (25 mg/kg), or vehicle. The tumor volume ($mm^3$) from tumor measurement was calculated: (Length*(Width/ $2)^2 * \pi$). Mice were sacrificed when the average tumor volume of the group reached 1500 $mm^3$.

Figure 7:
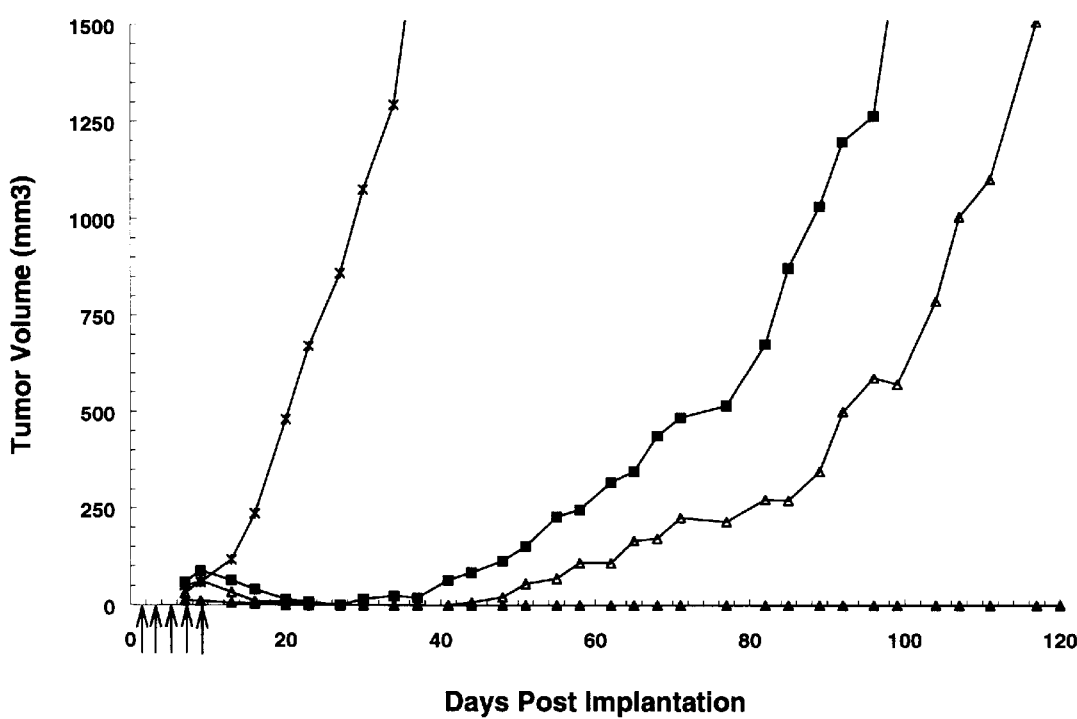
FIG. 7 Effect of BrC16HT administered iv. against sc. OVCAR-3 human ovarian cancer. C.B-17 SCID female mice (5/group) were inoculated with 2×10⁶ OVCAR-3 cells sc. and were treated iv. on days 1, 3, 5, 7 & 9 with (Δ) BrC16HT 12.5 mg/kg, (▲) BrC16HT 25 mg/kg, (■) Taxol® 25 mg/kg or (*) control.
Figure 8A:
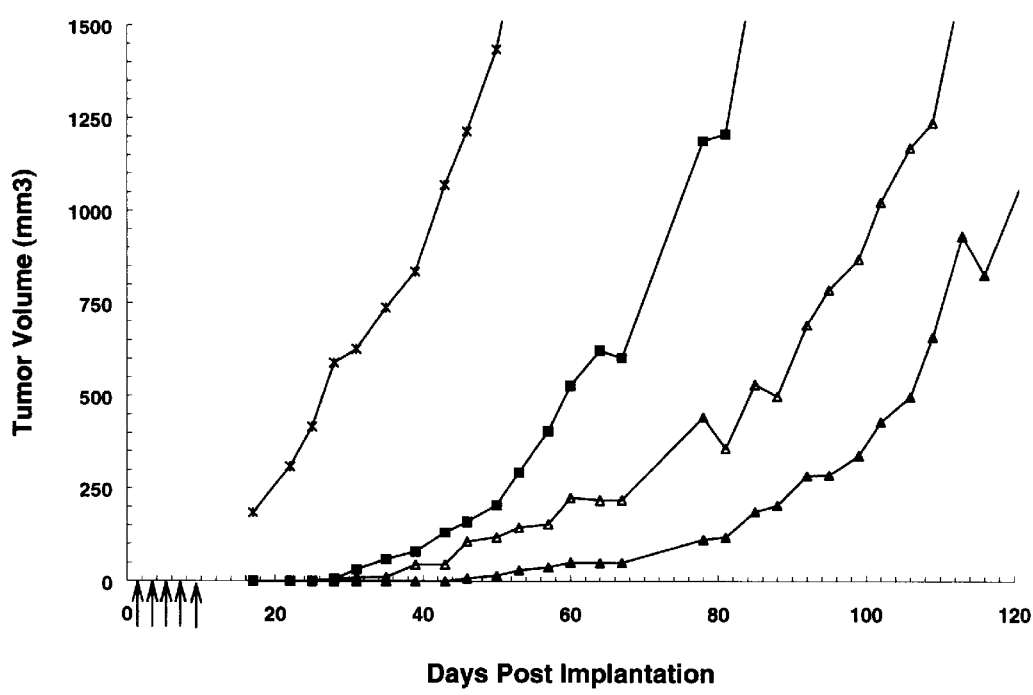
FIG. 8 Effect of BrC16HT administered iv. against sc. A549 human lung cancer. C.B-17 SCID female mice (5/group) were inoculated with 2×10⁶ A549 cells sc. and were treated iv. on days a) 1, 3, 5, 7 & 9, b) 1, 4, 7, 10 & 13, c) 1, 8, 15, 22 & 29 or d) 20, 22, 24, 26 & 28 with (A) BrC16HT 12.5 mg/kg, (▲) BrC16HT 25 mg/kg, (■) Taxol® 25 mg/kg or (*) control.
Figure 8B:
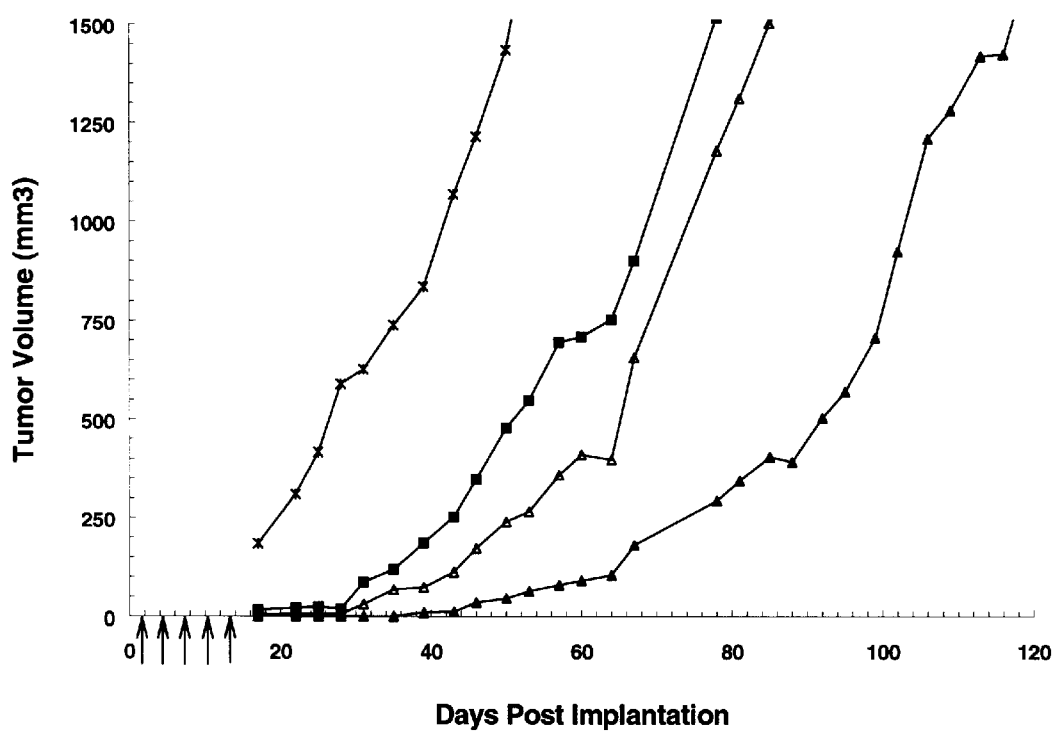
Figure 8C:
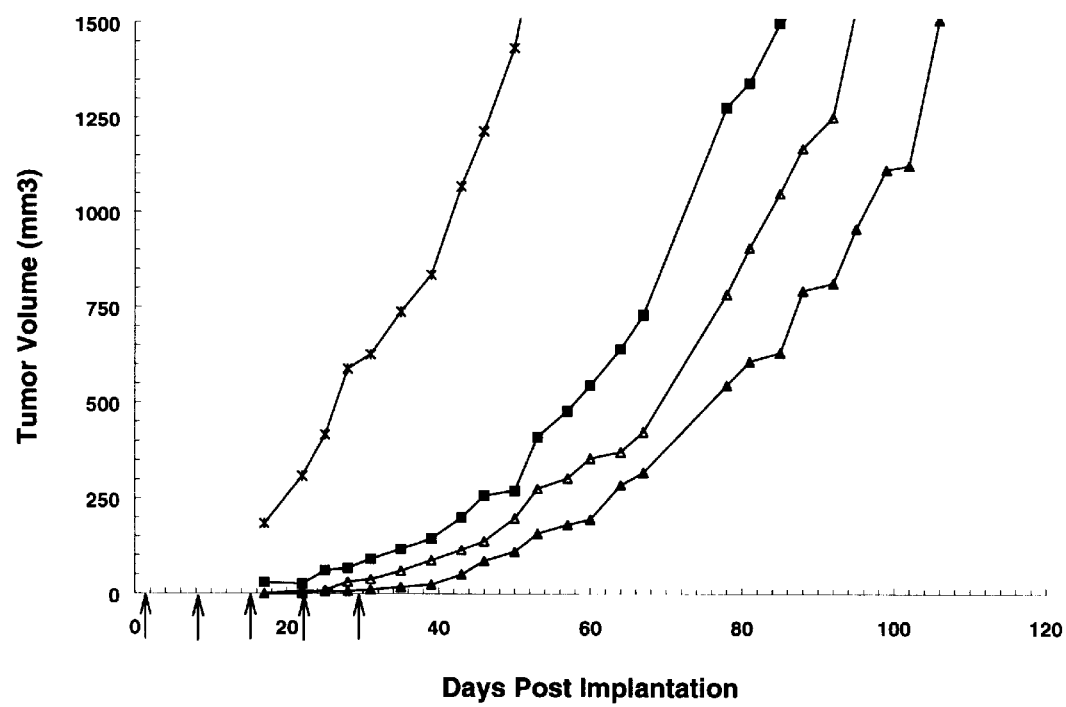
Figure 8D:
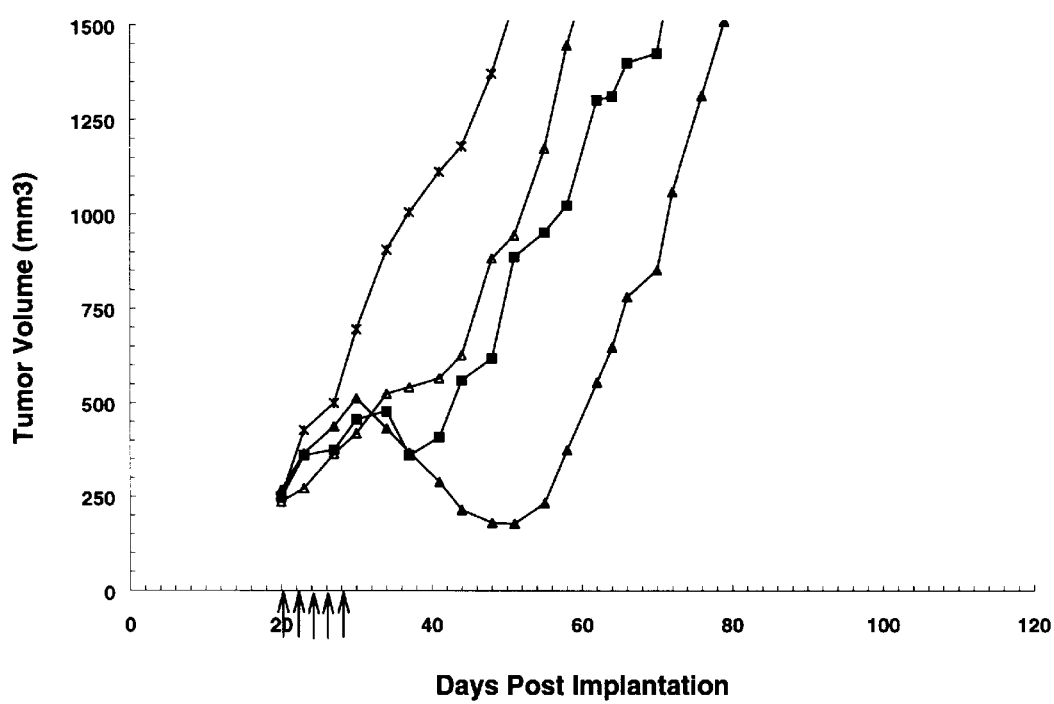

FIG. 7 shows that BrC16HT and Taxol® significantly ($p<0.05$ vs. control) inhibited the tumor growth of OVCAR-3 s.c. tumor in mice. BrC16HT at 12.5 mg/kg was more effective in delaying tumor growth than Taxol® 25 mg/kg (approximately 79 and 59 days respectively). BrC16HT at 25 mg/kg suppressed tumor growth completely up to 120 days post-implantation.

B. A549 Human NSCLC

1. I.p. Tumor, i.p. Treatment

SCID mice (6/group) were injected with $5 \times 10^6$ A549 human NSCLC cells i.p. (day 0). On days 1, 3, 5, 7 & 9 mice were treated i.p. with 12.5–50 mg/kg BrC16HT or 12.5 mg/kg Taxol.®

Table 10 shows that BrC16HT and Taxol® significantly ($p<0.05$ vs. control) increased the survival time of tumor-bearing mice. Five doses of BrC16HT at 12.5 mg/kg were as effective as Taxol® in the same dose schedule, with median survival times of 87 and 86 days respectively, whereas the higher doses of BrC16HT (25 or 50 mg/kg) that were able to be given further increased survival time in a dose-dependent manner, with median survival times of 112 and 171 days respectively.

TABLE 10

Effects of BrC16HT i.p. Against i.p. A549 Tumor Treatment days: 1, 3, 5, 7 and 9

| Treatment Group | Dose (mg/kg) | MST Days ± SEM | % ILS | Median | LTS/n |
|---|---|---|---|---|---|
| Control | Crem/EtOH | 34 ± 5 | — | 36 | 0/6 |
| Taxol | 12.5 | 89 ± 5 | 163 | 86 | 0/6 |
| BrC16HT | 12.5 | 87 ± 4 | 156 | 87 | 0/6 |
| BrC16HT | 25 | 117 ± 8 | 247 | 112 | 0/6 |
| BrC16HT | 50 | 186 ± 30 | 450 | 171 | 0/6 |

2. S.c. Tumor, i.v. Treatment

For solid tumor study, SCID mice (5/group) were injected s.c. with $2 \times 10^6$ A549 cells (day 0). On days 1, 3, 5, 7 & 9 or 1, 4, 7, 10 & 13 or 1, 8, 15, 22 & 29 or 20, 22, 24, 26 & 28, mice were treated i.v. with 12.5–25 mg/kg BrC16HT or 25 mg/kg Taxol.® The % ILS from survival data or the tumor volume was calculated as described above. Mice were sacrificed when the average tumor volume of the group reached 1500 $mm^3$.

FIG. 8 shows that BrC16HT and Taxol® significantly ($p<0.05$ vs. control) inhibited the tumor growth of A549 solid (s.c.) tumor in mice, independent of the dose schedule. However generally the earlier the treatment began and the closer the spacing of the five doses, the greater was the delay in tumor growth. In all early treatment schedules (FIGS. 8a–c) BrC16HT at 12.5 or 25 mg/kg was more effective than Taxol® at 25 mg/kg. For the delayed treatment schedule (FIG. 8d), treated on days 20, 22, 24, 26, and 28 there was greater and more prolonged tumor regression with BrC16HT than with Taxol® at the 25 mg/kg dose level.

Hydrophobic bromotaxol compositions comprising the hydrophobic taxane derivative in a non-liposomal lipid carrier, such polyoxyethylated derivative of castor oil (USP/NF Polyoxyl 35 Castor Oil) may also be administered to effectively treat a variety of cancers and inflammatory diseases such as arthritis.

Example 10

Formulation of 2'-(R)-[2-bromohexadecanoyl] Paclitaxel

2'-(R)-[2-bromohexadecanoyl] paclitaxel (BrC16HT) is formulated in Cremophor-ELP®. A sugar such as maltose may be added. One may lyophilize the formulation and after storage, reconstitute to the desired drug concentration with sterile water or any other pharmaceutically acceptable excipient.

600 mg of BrC16HT is dissolved in 20 ml of Cremophor-ELP®. The mixture is stirred for about 90 minutes at 30–35 degrees centigrade. (Solution 1)

Sterile water for injection was added to 14.5 grams of maltose monohydrate to give a solution volume of 160 ml. ®. The mixture is stirred for about 15 minutes at 30–35 degrees centigrade, and sterile filtered using a 0.22 µm (PVDF) type, hydrophilic filter. (Solution 2)

Solution 2 was added to Solution 1, and stirred at 30–35° C. for approximately 15 minutes. This solution was then sterile filtered using a 0.22 µm (PVDF) type, hydrophilic filter.

The formulation may additionally be lyophilized to provide an even longer shelf life. In one embodiment, 9 ml of Solution 3 was filled into each 20 ml, Type I, tubing vials. Lyophilization stoppers were placed on the vials, and the vials loaded into the freeze drying chamber. The lyophilization cycle program was started. When drying was complete, the chamber was backfilled with nitrogen, and the stoppers lowered. The vials were unloaded and sealed with aluminum caps.

Reconstitution was performed using sterile water for injection. A final active drug concentration of 3 mg/ml Br-HTD required approximately 8.5 ml of sterile water for injection per vial.

Final reconstituted concentrations:

3 mg/ml Br-HTD.

80 mg/ml maltose.

111 mg/ml cremophor EL-P . . . (Solution 1)

Example 11

Stability of BRC16HT in Various Formulations

Brc16HT formulations were prepared at 6 mg/ml or 20 mg/mL in Cremophor EL® :Ethanol (50:50 v/v). The 20 mg/mL formulation was further diluted to 6 mg/mL in 5% dextrose. The stability of the BrC16HT formulations was determined after storage at 4 or 26° C. by HPLC analysis. At 0 h, 24 h, 1, 2, 3, 4, and 5 weeks samples were chromatographically analyzed by diluting the drugs to 1 mg/mL with 5% dextrose and then mixing 1:1 with acetonitrile. The chromatographic system consisted of a Shimadzu LC100 system with a UV detector. The column used was an Inertsil-ODS 2, 150×4.6 mm (5 micron particle size) from Keystone Scientific (Bellefonte, Pa.). 20 μL of each sample were injected and read at 227 nm at ambient temperature. The standard curve was linear ($R^2$=0.998), from 6.25–100 μg/mL. The mobil phase consisted of water/acetonitrile (75%/25%) and acetonitrile (100%), and the gradient was: 70/30 (5 min), 30/70 (5 min), 0/100 (5 min), hold (5 min), 40/60 (5 min), and 70/30 (5 min) to equilibrate. The constant flow rate was 1 mL/min. The results are shown in the following table:

TABLE 11

Stability of BrC16HT in Cremophor Compositions

| Formulations (volume Ratio) | Final Conc. | Storage Temp ° C. | Percentage of BrC16HT in Sample | | | | | |
|---|---|---|---|---|---|---|---|---|
| | | | 0 h | 24 h | 1 Week | 2 Week | 3 Week | 4 Week | 5 Week |
| 6 mg/mL in Crem/EtOH (50–50) | 6 mg/mL[a] | 4 | 93 | 89 | 83 | 93 | 61 | 58 | 53 |
| 6 mg/mL in Crem/EtOH (50–50) | 6 mg/mL | 26 | 95 | 84 | 42 | 22 | 14 | 8 | 5 |
| 20 mg/mL in Crem/EtOH (50–50) | 6 mg/mL[b] | 4 | 92 | 91 | 90 | 88 | 83 | 85 | 82 |
| 20 mg/mL in Crem/EtOH (50–50) | 6 mg/mL | 26 | 97 | 99 | 93 | 90 | 81 | 88 | 87 |

[a]Undiluted
[b]Diluted with 5% dextrose to final concentration

The results shown on Table 11 above demonstrate that the stability of BrC16HT upon storage at about either 4° C. or 26° C. is increased when there is less cremophor in the storage sample. Comparison of the BrC16HT percentage remaining in the samples after 5 weeks in storage at either 4° C. or 26° C. demonstrates that the samples that were diluted from 20 mg/ml cremophor:ethanol to 6 mg/ml with dextrose (giving a final cremophor concentration of about 17%) contained more of the BrC16HT than those stored in 50% cremophor.

One skilled in the art will readily appreciate the present invention is well adapted to carry out the objects and obtain the ends and advantages mentioned, as well as those inherent therein. The compounds, compositions, methods, procedures and techniques described herein are presented as representative of the preferred embodiments, or intended to be exemplary and not intended as limitations on the scope of the present invention. Changes therein and other uses will occur to those of skill in the art that are encompassed within the spirit of the appended claims.

What is claimed is:

1. A taxane having the formula:

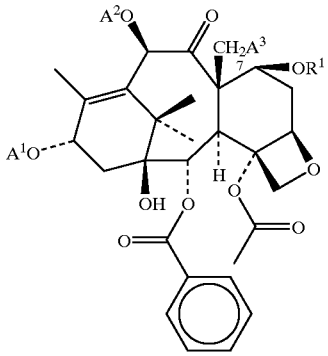

wherein:

$A^1$ is H or a group having the formula Z—C(O)NHCH($C_6H_5$)CH(OR) —C(O)—, $A^2$ is H or $CH_3C(O)$— and $A^3$ is H or OH;

Z is $C_6H_5$—, $C_6H_5CH_2$—O—, $C(CH_3)_3$—O— or $CH(CH_3)$=$C(CH_3)$—;

each of R and $R^1$ is H or a group having the formula $Y^1Y^2$, provided that at least one of R and $R^1$ is not H;

$Y^1$ is a group having the formula —C(O)CHX$^1$(CH$_2$)$_{n1}$(CH=CH)$_{n2}$(CH$_2$)$_{n3}$(CH=CH)$_{n4}$(CH$_2$)$_{n5}$(CH=CH)$_{n6}$(CH$_2$)$_{n7}$(CH=CH)$_{n8}$(CH$_2$)$_{n9}$—;

the sum of n1+2n2+n3+2n4+n5+2n6+n7+2n8+n9 is an integer of from 1 to 21, each of n2, n4, n6 and n8 is independently zero or 1, n1 is zero or an integer of from 1 to 21, n3 is zero or an integer of from 1 to 18, n5 is zero or an integer of from 1 to 15, n7 is zero or an integer of from 1 to 12, n9 is zero or an integer of from 1 to 9 and each of n1 to n9 can be the same or different at each occurrence;

$X^1$ is an hydrolysis-promoting group; and $Y^2$ is —$CH_3$, —$CO_2H$ or —$CH_2OH$;

wherein the carbon to which the $X^1$ is attached has a stereospecific configuration selected from the group consisting of an (R) configuration, an (S) configuration and a mixture of (R) and (S) configurations.

2. The taxane of claim 1, wherein $A^1$ is a group having the formula Z—C(O)NHCH($C_6H_5$)CH(OR)C(O)—.

3. The taxane of claim 2, wherein $R^1$ is H.

4. The taxane of claim 3, wherein R is a group having the formula $Y^1CH_3$.

5. The taxane of claim 4, wherein R is —C(O)CHX$^1$(CH$_2$)$_3$CH$_3$, —C(O)CHX$^1$(CH$_2$)$_5$CH$_3$, —C(O)CHX$^1$(CH$_2$)$_9$CH$_3$, —C(O)CHX$^1$(CH$_2$)$_{11}$CH$_3$, or —C(O)CHX$^1$(CH$_2$)$_{13}$CH$_3$.

6. The taxane of claim 2, wherein R is H.

7. The taxane of claim 6, wherein $R^1$ is a group having the formula $Y^1CH_3$.

8. The taxane of claim 7, wherein $R^1$ is —C(O)CHX$^1$(CH$_2$)$_3$CH$_3$, —C(O)CHX$^1$(CH$_2$)$_5$CH$_3$, —C(O)CHX$^1$(CH$_2$)$_9$CH$_3$, or —C(O)CHX$^1$(CH$_2$)$_{13}$CH$_3$.

9. The taxane of claim 1, wherein $X^1$ is F, Cl, Br, I, the group —OC$_6$H$_4$X$^2$ or the group —C(O)X$^2$ and wherein $X^2$ is F, Cl, Br, I, CN, NO$_2$ or NH$_3^+$.

10. The taxane of claim 2, wherein Z is $C_6H_5$.

11. The taxane of claim 10, wherein $A^2$ is $CH_3C(O)$— and wherein $A^3$ is H.

12. The taxane of claim 11, wherein $R^1$ is H and R is —C(O)CHX$^1$(CH$_2$)$_3$CH$_3$, —C(O)CHX$^1$(CH$_2$)$_5$CH$_3$, —C(O)CHX$^1$(CH$_2$)$_9$CH$_3$, —C(O)CHX$^1$(CH$_2$)$_{11}$CH$_3$, or —C(O)CHX$^1$(CH$_2$)$_{13}$CH$_3$.

13. The taxane of claim 12, wherein $X^1$ is F, Cl, Br or I.

14. The taxane of claim 11, wherein $R^1$ is H and R is —C(O)CHX$^1$(CH$_2$)$_3$CH$_3$, —C(O)CHX$^1$(CH$_2$)$_5$CH$_3$, —C(O)CHX$^1$(CH$_2$)$_9$CH$_3$, —C(O)CHX$^1$(CH$_2$)$_{11}$CH$_3$, or —C(O)CHX$^1$(CH$_2$)$_{13}$CH$_3$.

15. The taxane of claim 14, wherein $X^1$ is F, Cl, Br or I.

16. The taxane of any one of claims 1 to 15 wherein the carbon to which the $X^1$ is attached has an (R) configuration.

17. The taxane of any one of claims 1 to 15 wherein the carbon to which the $X^1$ is attached has an (S) configuration.

18. The taxane of any one of claims 1 to 15 wherein the carbon to which the $X^1$ is attached has a mixture of (S) and (R) configurations.

19. A composition comprising the taxane of claim 1 and a pharmaceutically acceptable medium.

20. The composition of claim 19, wherein the pharmaceutically acceptable medium comprises a polyoxyethylated derivative of castor oil.

21. The composition of claim 20, wherein the weight ratio of taxane to a polyoxyethylated derivative of castor oil is from about 13 to about 30 parts per thousand.

22. The composition of claim 20, wherein the sum of n1+2n2+n3+2n4+n5+2n6+n7+2n8+n9 is an integer of from 3 to 21.

23. The composition of claim 22, wherein the sum of n1+2n2+n3+2n4+n5+2n6+n7+2n8+n9 is an integer of from 9 to 21.

24. The composition of claim 23, wherein the sum of n1+2n2+n3+2n4+n5+2n6+n7+2n8+n9 is an integer of from 13 to 21.

25. The composition of claim 20, wherein $Y^1$ is —C(O)CHBr(CH$_2$)$_{13}$CH$_3$.

26. A method of administering a taxane to an animal which comprises administering to the animal a treatment effective dose of a composition comprising the taxane of claim 1 and a pharmaceutically acceptable carrier.

27. The method of claim 26, wherein the pharmaceutically acceptable carrier is comprises a polyoxyethylated derivative of castor oil.

28. The method of claim 27, wherein the animal is afflicted with a cancer and wherein an anticancer effective amount of the taxane is administered.

29. The method of claim 28, wherein the anticancer effective amount of the taxane is from about 0.1 mg per kg of body weight of the animal to about 1000 mg per kg.

30. The method of claim 26, wherein $A^1$ is a group having the formula —C$_6$H$_5$C(O)NHCH(C$_6$H$_5$)CH(OR)C(O)—, $A^2$ is —CH$_3$C(O)—, $A^3$ is H and one of R or $R^1$ is —C(O)CHX$^1$(CH$_2$)$_3$CH$_3$, —C(O)CHX$^1$(CH$_2$)$_5$CH$_3$, —C(O)CHX$^1$(CH$_2$)$_9$CH$_3$, —C(O)CHX$^1$(CH$_2$)$_{11}$CH$_3$ or —C(O)CHX$^1$(CH$_2$)$_{13}$CH$_3$.

31. The method of claim 28, wherein the cancer is a lung, colon, brain, stomach, breast, ovarian, or prostate cancer or a cancer of the head and neck, or a leukemia, lymphoma, sarcoma or carcinoma.

32. The method of claim 26, wherein the composition is an inflammatory disease treating effective amount or an inflammatory disease prophylactic effective amount of the composition of claim 1.

33. The method of claim 32 wherein the inflammatory disease is arthritis.

34. The method of claim 26, comprising administering an additional bioactive agent to the animal.

35. A taxane having the formula:

wherein:

$A^1$ is H or a group having the formula Z—C(O)NHCH(C$_6$H$_5$)CH(OR) —C(O)—, $A^2$ is H or CH$_3$C(O)— and $A^3$ is H or OH;

Z is C$_6$H$_5$—, C$_6$H$_5$CH$_2$—O—, C(CH$_3$)$_3$—O— or CH(CH$_3$)=C(CH$_3$)—;

each of R and $R^1$ is H or a group having the formula $Y^1Y^2$, provided that at least one of R and $R^1$ is not H;

$Y^1$ is a group having the formula —C(O)CHX$^1$(CH$_2$)$_{n1}$(CH=CH)$_{n2}$(CH$_2$)$_{n3}$(CH=CH)$_{n4}$(CH$_2$)$_{n5}$(CH=CH)$_{n6}$(CH$_2$)$_{n7}$(CH=CH)$_{n8}$(CH$_2$)$_{n9}$—;

the sum of n1+2n2+n3+2n4+n5+2n6+n7+2n8+n9 is an integer of from 1 to 21, each of n2, n4, n6 and n8 is independently zero or 1, n1 is zero or an integer of from 1 to 21, n3 is zero or an integer of from 1 to 18, n5 is zero or an integer of from 1 to 15, n7 is zero or an integer of from 1 to 12, n9 is zero or an integer of from 1 to 9 and each of n1 to n9 can be the same or different at each occurrence;

$X^1$ is an hydrolysis-promoting group; and $Y^2$ is —$CH_3$, —$CO_2H$ or —$CH_2OH$;
wherein the carbon to which the $X^1$ is attached has a stereospecific configuration resulting in a positive or negative specific rotation.

36. The taxane of claim 35, wherein $A^1$ is a group having the formula Z—C(O)NHCH($C_6H_5$)CH(OR)C(O)—.

37. The taxane of claim 36, wherein $R^1$ is H.

38. The taxane of claim 37, wherein R is a group having the formula $Y^1CH_3$.

39. The taxane of claim 38, wherein R is —C(O)$CHX^1$($CH_2$)$_3CH_3$, —C(O)$CHX^1$($CH_2$)$_5CH_3$, —C(O)$CHX^1$($CH_2$)$_9$ $CH_3$, —C(O)$CHX^1$($CH_2$)$_{11}CH_3$, or —C(O)$CHX^1$($CH_2$)$_{13}$ $CH_3$.

40. The taxane of claim 36, wherein R is H.

41. The taxane of claim 40, wherein $R^1$ is a group having the formula $Y^1CH_3$.

42. The taxane of claim 41, wherein $R^1$ is —C(O)$CHX^1$($CH_2$)$_3CH_3$, —C(O)$CHX^1$($CH_2$)$_5CH_3$, —C(O)$CHX^1$($CH_2$)$_9$ $CH_3$, or —C(O)$CHX^1$($CH_2$)$_{13}CH_3$.

43. The taxane of claim 35, wherein $X^1$ is F, Cl, Br, I, the group —$OC_6H_4X^2$ or the group —C(O)$X^2$ and wherein $X^2$ is F, Cl, Br, I, CN, $NO_2$ or $NH_3^+$.

44. The taxane of claim 36, wherein Z is $C_6H_5$.

45. The taxane of claim 44, wherein $A^2$ is $CH_3$C(O)— and wherein $A^3$ is H.

46. The taxane of claim 45, wherein $R^1$ is H and R is —C(O)$CHX^1$($CH_2$)$_3CH_3$, —C(O)$CHX^1$($CH_2$)$_5CH_3$, —C(O)$CHX^1$($CH_2$)$_9CH_3$, —C(O)$CHX^1$($CH_2$)$_{11}CH_3$, or —C(O)$CHX^1$($CH_2$)$_{13}CH_3$.

47. The taxane of claim 46, wherein $X^1$ is F, Cl, Br or I.

48. The taxane of claim 45, wherein $R^1$ is H and R is —C(O)$CHX^1$($CH_2$)$_3CH_3$, —C(O)$CHX^1$($CH_2$)$_5CH_3$, —C(O)$CHX^1$($CH_2$)$_9CH_3$, —C(O)$CHX^1$($CH_2$)$_{11}CH_3$, or —C(O)$CHX^1$($CH_2$)$_{13}CH_3$.

49. The taxane of claim 48, wherein $X^1$ is F, Cl, Br or I.

50. The taxane of claim 35 wherein the carbon to which the $X^1$ is attached has a positive specific rotation.

51. The taxane of claim 49 wherein the carbon to which the $X^1$ is attached has a positive specific rotation.

52. The taxane of claim 35 wherein the carbon to which the $X^1$ is attached has a negative specific rotation.

53. The taxane of claim 49 wherein the carbon to which the $X^1$ is attached has a negative specific rotation.

54. A composition comprising the taxane of claim 35 and a pharmaceutically acceptable medium.

55. The composition of claim 54, wherein the pharmaceutically acceptable medium comprises a polyoxyethylated derivative of castor oil.

56. The composition of claim 55, wherein the weight ratio of taxane to a polyoxyethylated derivative of castor oil is from about 13 to about 30 parts per thousand.

57. The composition of claim 55, wherein the sum of n1+2n2+n3+2n4+n5+2n6+n7+2n8+n9 is an integer of from 3 to 21.

58. The composition of claim 57, wherein the sum of n1+2n2+n3+2n4+n5+2n6+n7+2n8+n9 is an integer of from 9 to 21.

59. The composition of claim 58, wherein the sum of n1+2n2+n3+2n4+n5+2n6+n7+2n8+n9 is an integer of from 13 to 21.

60. The composition of claim 55, wherein $Y^1$ is —C(O)CHBr($CH_2$)$_{13}CH_3$.

61. A method of administering a taxane to an animal which comprises administering to the animal a treatment effective dose of a composition comprising the taxane of claim 35 and a pharmaceutically acceptable carrier.

62. The method of claim 61, wherein the pharmaceutically acceptable carrier is comprises a polyoxyethylated derivative of castor oil.

63. The method of claim 62, wherein the animal is afflicted with a cancer and wherein an anticancer effective amount of the taxane is administered.

64. The method of claim 63, wherein the anticancer effective amount of the taxane is from about 0.1 mg per kg of body weight of the animal to about 1000 mg per kg.

65. The method of claim 61, wherein $A^1$ is a group having the formula
—$C_6H_5$C(O)NHCH($C_6H_5$)CH(OR)C(O)—, $A^2$ is —$CH_3$C(O)—, $A^3$ is H and one of R or $R^1$ is —C(O)$CHX^1$($CH_2$)$_3CH_3$, —C(O)$CHX^1$($CH_2$)$_5CH_3$, —C(O)$CHX^1$($CH_2$)$_9CH_3$, —C(O)$CHX^1$($CH_2$)$_{11}CH_3$ or —C(O)$CHX^1$($CH_2$)$_{13}CH_3$.

66. The method of claim 63, wherein the cancer is a lung, colon, brain, stomach, breast, ovarian, or prostate cancer or a cancer of the head and neck, or a leukemia, lymphoma, sarcoma or carcinoma.

67. The method of claim 61, wherein the composition is an inflammatory disease treating effective amount or an inflammatory disease prophylactic effective amount of the composition of claim 35.

68. The method of claim 67 wherein the inflammatory disease is arthritis.

69. The method of claim 61, comprising administering an additional bioactive agent to the animal.

* * * * *

UNITED STATES PATENT AND TRADEMARK OFFICE
CERTIFICATE OF CORRECTION

PATENT NO. : 6,107,332
DATED : 08/22/00
INVENTOR(S) : Shaukat Ali, J. Craig Franklin, Imran Ahmad, Eric Mayhew, Soumendo Bhattacharya, It is certified that error appears in the above-identified patent and that said Letters Patent is hereby corrected as shown below:

On the title page, please change the spelling of the name of inventor "Gil Koehane" to read --Gil Keohane--.

Signed and Sealed this

Twenty-ninth Day of May, 2001

*Attest:*

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO.   : 6,107,332
DATED        : August 22, 2000
INVENTOR(S)  : Ali et al.

It is certified that error appears in the above-identified patent and that said Letters Patent is hereby corrected as shown below:

Column 18,
Delete last chain formula, and substitute therefore

Line 53, after "2'" delete "(R)".
Line 54, after "2'-" delete "(R)-.

Column 19,
The 1st chain formula, delete "O" and insert -- OH --

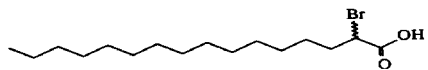

The 4th and 5th chain formulas delete "H$_3$" and insert -- CH$_3$ --
The 6th and 7th chain formuals delete "H$_3$" and insert -- CH$_3$ --

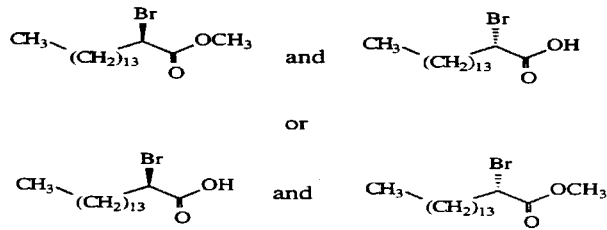

Column 20,
Line 60, delete "-(R)"-.
Line 61, delete "taxol" and insert -- paclitaxel" --.
Line 62, delete "Bromohexanoyl" and insert -- Bromohexdecanoyl --.
Line 62, delete "taxol" and insert -- paclitaxel --.

UNITED STATES PATENT AND TRADEMARK OFFICE
CERTIFICATE OF CORRECTION

PATENT NO. : 6,107,332 B1
DATED : August 22, 2000
INVENTOR(S) : Ali et al.

It is certified that error appears in the above-identified patent and that said Letters Patent is hereby corrected as shown below:

Column 29,
Line 21, delete "BRC16HT" and insert -- BrC16HT --.
Line 22, delete "Brc16HT" and insert -- BrC16HT --.

Signed and Sealed this

Twenty-first Day of January, 2003

JAMES E. ROGAN
*Director of the United States Patent and Trademark Office*